(12) United States Patent
Moloney et al.

(10) Patent No.: US 6,509,453 B1
(45) Date of Patent: *Jan. 21, 2003

(54) OIL BODIES AND ASSOCIATED PROTEINS AS AFFINITY MATRICES

(75) Inventors: Maurice Moloney, Calgary (CA); Joseph Boothe, Calgary (CA); Gijs Van Rooijen, Calgary (CA)

(73) Assignee: SemBioSys Genetics Inc., Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/319,275

(22) PCT Filed: Dec. 5, 1997

(86) PCT No.: PCT/CA97/00951

§ 371 (c)(1),
(2), (4) Date: Aug. 27, 1999

(87) PCT Pub. No.: WO98/27115

PCT Pub. Date: Jun. 25, 1998

Related U.S. Application Data

(63) Continuation-in-part of application No. 08/767,026, filed on Dec. 16, 1996, now Pat. No. 5,856,452.

(51) Int. Cl.[7] .................................................. C07K 1/00
(52) U.S. Cl. ........................ 530/412; 530/412; 530/350; 435/7.1; 435/172.3; 435/183; 435/6; 514/2; 514/12; 514/21
(58) Field of Search ................................ 435/183, 701, 435/172.3, 6, 69.1; 530/350, 412; 514/12, 2, 21

(56) References Cited

U.S. PATENT DOCUMENTS 5,474,925 A 12/1995 Maliyakal et al. ........ 435/172.3
5,538,946 A 7/1996 Crause et al. ................. 514/12
5,856,452 A * 1/1999 Moloney et al. ............ 530/412

FOREIGN PATENT DOCUMENTS

WO WO 93/21320 10/1993
WO WO 96/21029 7/1996

OTHER PUBLICATIONS

Coughlin and Baclaski, *Biotechnology Progress*, 6:307–309, 1990.
Labrou and Clonis, *Journal of Biotechnology* 36: 95–119, 1994.
Ong et al., *Bioseparation*. 5:95–104, 1995.
Paradkar et al., *Biotechnol. Prog.*, 7:330–334, 1991.
Paramenter et al., *Plant Molecular Biology*, 29: 1167–1180, 1995.
Pires et al., *Biotechnol. Prog.* 12:290–301, 1996.
Ramirez et al., *Biotechnology*, 11:1570–1573, 1993.
Schreuder et al., *TIBTECH*, vol. 14, 1996.
Van Rooijen and Moloney, *Plant Physiol* 109:1353–1361, 1995.
Van Rooijen, "Molecular Biology of Oil Body Proteins in the Brassicaceae: Structure, Function and Biotechnological Applications" Ph. D. thesis, 177–191.

* cited by examiner

Primary Examiner—Karen Cochrane Carlson
Assistant Examiner—Hope A. Robinson
(74) Attorney, Agent, or Firm—Bereskin & Parr; Micheline Gravelle

(57) ABSTRACT

A method for the separation of a target molecule from a mixture is described. The method employs oil bodies and their associated proteins as affinity matrices for the selective, non-covalent binding of desired target molecules. The oil body proteins may be genetically fused to a ligand having specificity for the desired target molecule. Native oil body proteins can also be used in conjunction with an oil body protein specific ligand such as an antibody or an oil body binding protein. The method allows the separation and recovery of the desired target molecules due to the difference in densities between oil bodies and aqueous solutions

28 Claims, 20 Drawing Sheets

FIGURE 1

```
  1 ATG GCG GAT ACA GCT AGA GGA ACC CAT CAC GAT ATC ATC GGC AGA GAC CAG TAC CCG ATG  60
  1 M   A   D   T   A   R   G   T   H   H   D   I   I   G   R   D   Q   Y   P   M    20

61 ATG GGC CGA GAC CGA GAC CAG TAC CAG ATG TCC GGA CGA GGA TCT GAC TAC TCC AAG TCT 120
 21 M   G   R   D   R   D   Q   Y   Q   M   S   G   R   G   S   D   Y   S   K   S    40

121 AGG CAG ATT GCT AAA GCT GCA ACT GCT GTC ACA GCT GGT GGT TCC CTC CTT GTT CTC TCC 180
 41 R   Q   I   A   K   A   A   T   A   V   T   A   G   G   S   L   L   V   L   S    60

181 AGC CTT ACC CTT GTT GGA ACT GTC ATA GCT TTG ACT GTT GCA ACA CCT CTG CTC GTT ATC 240
 61 S   L   T   L   V   G   T   V   I   A   L   T   V   A   T   P   L   L   V   I    80

241 TTC AGC CCA ATC CTT GTC CCG GCT CTC ATC ACA GTT GCA CTC CTC ATC ACC GGT TTT CTT 300
 81 F   S   P   I   L   V   P   A   L   I   T   V   A   L   L   I   T   G   F   L   100

301 TCC TCT GGA GGG TTT GGC ATT GCC GCT ATA ACC GTT TTC TCT TGG ATT TAC AAG TAC GCA 360
101 S   S   G   G   F   G   I   A   A   I   T   V   F   S   W   I   Y   K   Y   A   120

361 ACG GGA GAG CAC CCA CAG GGA TCA GAC AAG TTG GAC AGT GCA AGG ATG AAG TTG GGA AGC 420
121 T   G   E   H   P   Q   G   S   D   K   L   D   S   A   R   M   K   L   G   S   140

421 AAA GCT CAG GAT CTG AAA GAC AGA GCT CAG TAC TAC GGA CAG CAA CAT ACT GGT GGG GAA 480
141 K   A   Q   D   L   K   D   R   A   Q   Y   Y   G   Q   Q   H   T   G   G   E   160

481 CAT GAC CGT  GAC CGT ACT CGT GGT GGC CAG CAC ACT ACT TAA
161 H   D   R    D   R   T   R   G   G   Q   H   T   T   *
```

FIGURE 2A

```
   1 ctatacccaacctcggtcttggtcacaccaggaactctctggtaagctagctccactccccagaaacaaccggcgccaaa  80
  81 ttgccggaattgctgacctgaagacggaacatcatcgtcgggtccttgggcgattgcggcggaagatgggtcagcttggg 160
 161 cttgaggacgagacccgaatcgagtctgttgaaaggttgttcattgggatttgtatacggagattggtcgtcgagaggtt 240
 241 tgagggaaaggacaaatgggtttggctctggagaaagagagtgcggctttagagagagaattgagaggtttagagagaga 320
 321 tgcggcggcgatgacgggaggagagacgacgaggacctgcattatcaaagcagtgacgtggtgaaatttggaacttttaa 400
 401 gaggcagatagatttattatttgtatccatttt cttcattgttctagaatgtcgcggaacaaattttaaaactaaatcct 480
 481 aaatttttctaatttt gttgccaatagtggatatgtgggccgtatagaaggaatctattgaaggcccaaacccatactga 560
 561 cgagcccaaaggttcgttttgcgttttatgtttcggttcgatgccaacgccacattctgagctaggcaaaaaacaaacgt 640
 641 gtctttgaatagactcctctcgttaacacatgcagcggctgcatggtgacgccattaacacgtggcctacaattgcatga 720
 721 tgtctccattgacacgtgacttctcgtctcctttcttaatatatctaacaaacactcctacctcttccaaaatatataca 800
 801 catcttttgatcaatctctcattcaaaatctcattctctctagtaaacaagaacaaaaaa ATG GCG GAT ACA      873
   1                                                              M   A   D   T        4

874 GCT AGA GGA ACC CAT CAC GAT ATC ATC GGC AGA GAC CAG TAC CCG ATG ATG GGC CGA GAC  933
   5  A   R   G   T   H   H   D   I   I   G   R   D   Q   Y   P   M   M   G   R   D   24

934 CGA GAC CAG TAC CAG ATG TCC GGA CGA GGA TCT GAC TAC TCC AAG TCT AGG CAG ATT GCT  993
  25  R   D   Q   Y   Q   M   S   G   R   G   S   D   Y   S   K   S   R   Q   I   A   44

994 AAA GCT GCA ACT GCT GTC ACA GCT GGT GGT TCC CTC CTT GTT CTC TCC AGC CTT ACC CTT 1053
  45  K   A   A   T   A   V   T   A   G   G   S   L   L   V   L   S   S   L   T   L   64

1054 GTT GGA ACT GTC ATA GCT TTG ACT GTT GCA ACA CCT CTG CTC GTT ATC TTC AGC CCA ATC 1113
  65  V   G   T   V   I   A   L   T   V   A   T   P   L   L   V   I   F   S   P   I   84

1114 CTT GTC CCG GCT CTC ATC ACA GTT GCA CTC CTC ATC ACC GGT TTT CTT TCC TCT GGA GGG 1173
  85  L   V   P   A   L   I   T   V   A   L   L   I   T   G   F   L   S   S   G   G  104

1174 TTT GGC ATT GCC GCT ATA ACC GTT TTC TCT TGG ATT TAC AA gtaagcacacatttatcatcttact 1239
 105  F   G   I   A   A   I   T   V   F   S   W   I   Y   K                           118

1240 tcataattttgtgcaatatgtgcatgcatgtgttgagccagtagctttggatcaattttttt ggtcgaataacaaatgta 1319

1320 acaataagaaattgcaaattctagggaacatttggttaactaaatacgaaatttgacctagctagcttgaatgtgtctgt 1399

1400 gtatatcatctatataggtaaaatgcttggtatgataccta ttgattgtgaatag G TAC GCA ACG GGA GAG   1470
 119                                                           Y   A   T   G   E      123
```

FIGURE 2B

```
1471 CAC CCA CAG GGA TCA GAC AAG TTG GAC AGT GCA AGG ATG AAG TTG GGA AGC AAA GCT CAG 1530
 124 H   P   Q   G   S   D   K   L   D   S   A   R   M   K   L   G   S   K   A   Q   143

1531 GAT CTG AAA GAC AGA GCT CAG TAC TAC GGA CAG CAA CAT ACT GGT TGG GAA CAT GAC CGT 1590
 144 D   L   K   D   R   A   Q   Y   Y   G   Q   Q   H   T   G   W   E   H   D   R   163

1591 GAC CGT ACT CGT GGT GGC CAG CAC ACT ACT GCG ATC GAA GGG AGA ATC ACT TAC ACT GAC 1650
 164 D   R   T   R   G   G   Q   H   T   T   A   I   E   G   R   I   T   Y   T   D   183

1651 TGT ACT GAA TCT GGA CAG AAC CTC TGT CTC TGT GAA GGA TCT AAC GTT TGT GGA AAG GGA 1710
 184 C   T   E   S   G   Q   N   L   C   L   C   E   G   S   N   V   C   G   K   G   203

1711 AAC AAG TGT ATC CTC GGA TCT AAC GGA AAG GGA AAC CAG TGT GTT ACT GGA GAA GGA ACT 1770
 204 N   K   C   I   L   G   S   N   G   K   G   N   Q   C   V   T   G   E   G   T   223

1771 CCA AAC CCA GAA TCT CAC AAC AAC GGA GAC TTC GAA GAA ATC CCT GAA GAA TAC CTC CAG 1830
 224 P   N   P   E   S   H   N   N   G   D   F   E   E   I   P   E   E   Y   L   Q   243

1831 TAA gtcgactctagacggatctcccgatcgttcaaacatttggcaataaagtttcttaagattgaatcctgttgccggt 1909
 244 *                                                                                244

1910 cttgcgatgattatcatataatttctgttgaattacgttaagcatgtaataattaacatgtaatgcatgacgttatttat 1989

1990 gagatgggttttatgattagagtcccgcaattatacatttaatacgcgatagaaaacaaaatatagcgcgcaaactagg 2069

2070 ataaattatcgcgcgcggtgtcatctatgttactagatcGGAATTC                                    2115
```

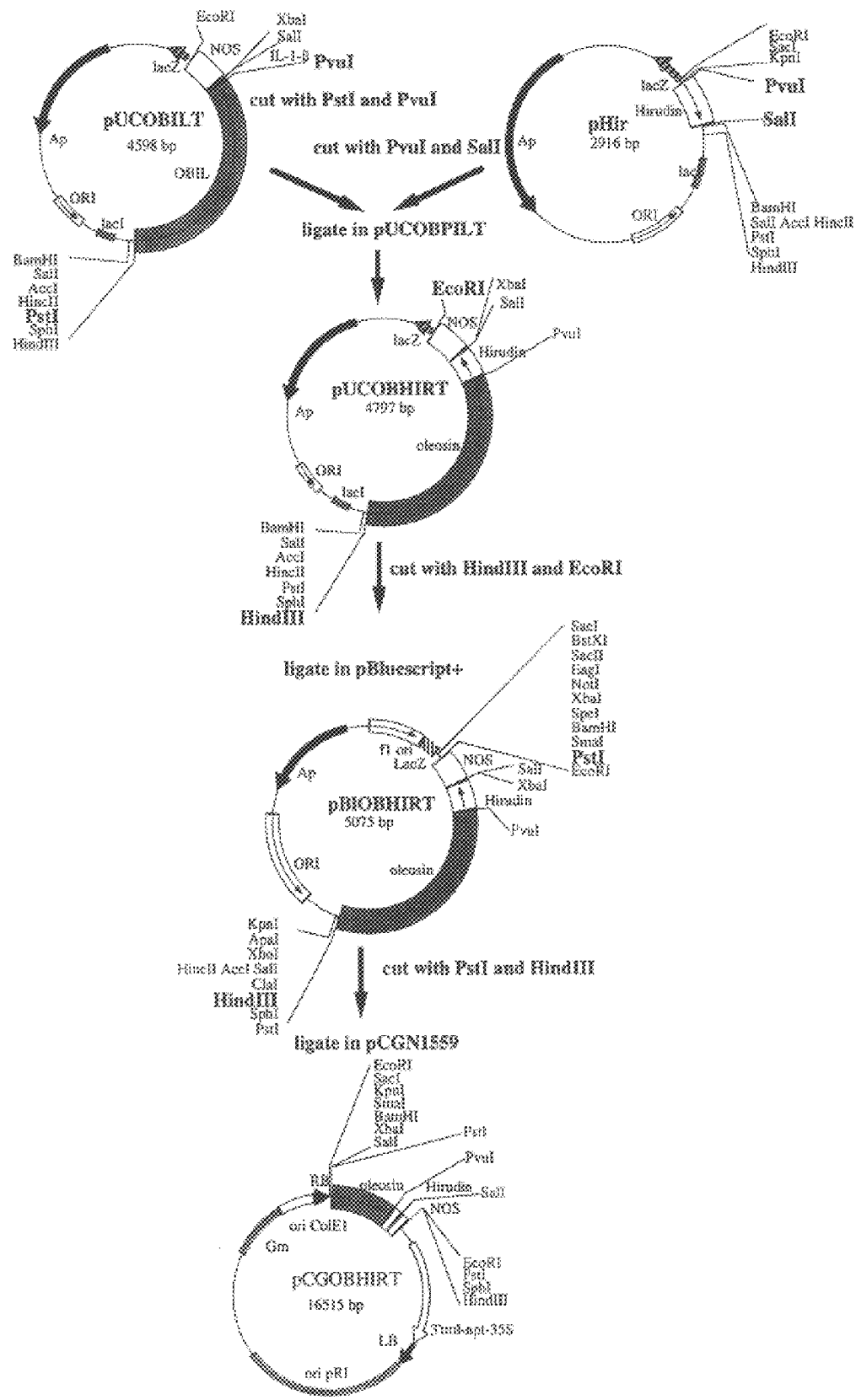

FIGURE 8A

```
   1 gagctcaaatacgatctgatactgataacgtctagattttagggttaaagcaatcaatcacctgacgattcaaggtggt   80
  81 tggatcatgacgattccagaaaacatcaagcaagctctcaaagctacactctttgggatcatactgaactctaacaacct  160
 161 cgttatgtcccgtagtgccagtacagacatcctcgtaactcggattatgcacgatgccatggctatacccaacctcggtc  240
 241 ttggtcacaccaggaactctctggtaagctagctccactccccagaaacaaccggcgccaaattgccggaattgctgacc  320
 321 tgaagacggaacatcatcgtcgggtccttgggcgattgcggcggaagatgggtcagcttgggcttgaggacgagacccga  400
 401 atcgagtctgttgaaaggttgttcattgggatttgtatacggagattggtcgtcgagaggtttgagggaaaggacaaatg  480
 481 ggtttggctctggagaaagagagtgcggctttagagagagaattgagaggtttagagagagatgcggcggcgatgacggg  560
 561 aggagagacgacgaggacctgcattatcaaagcagtgacgtggtgaaatttggaacttttaagaggcagatagatttatt  640
 641 atttgtatccatttctcattgttctagaatgtcgcggaacaaattttaaaactaaatcctaaatttttctaattttgt   720
 721 tgccaatagtggatatgtgggccgtatagaaggaatctattgaaggcccaaacccatactgacgagcccaaaggttcgtt  800
 801 ttgcgttttatgtttcggttcgatgccaacgccacattctgagctaggcaaaaaacaaacgtgtctttgaatagactcct  880
 881 ctcgttaacacatgcagcggctgcatggtgacgccattaacacgtggcctacaattgcatgatgtctccattgacacgtg  960
 961 acttctcgtctcctttcttaatatatctaacaaacactcctacctcttccaaaatatatacacatcttttgatcaatct 1040
1041 ctcattcaaaatctcattctctctagtaaacaggatcccctcgcggccgc ATG GCG GAT ACA GCT AGA ACC 1112
   1                                                   M   A   D   T   A   R   T    7
1113 CAT CAC GAT GTC ACA AGT CGA GAT CAG TAT CCC CGA GAC CGA GAC CAG TAT TCT ATG ATC 1172
   8  H   H   D   V   T   S   R   D   Q   Y   P   R   D   R   D   Q   Y   S   M   I   27
1173 GGT CGA GAC CGT GAC CAG TAC TCT ATG ATG GGC CGA GAC CGA GAC CAG TAC AAC ATG TAT 1232
  28  G   R   D   R   D   Q   Y   S   M   M   G   R   D   R   D   Q   Y   N   M   Y   47
1233 GGT CGA GAC TAC TCC AAG TCT AGA CAG ATT GCT AAG GCT GTT ACC GCA GTC ACG GCG GGT 1292
  48  G   R   D   Y   S   K   S   R   Q   I   A   K   A   V   T   A   V   T   A   G   67
1293 GGG TCC CTC CTT GTC CTC TCC AGT CTC ACC CTT GTT GGT ACT GTC ATT GCT TTG ACT GTT 1352
  68  G   S   L   L   V   L   S   S   L   T   L   V   G   T   V   I   A   L   T   V   87
1353 GCC ACT CCA CTC CTC GTT ATC TTT AGC CCA ATC CTC GTG CCG GCT CTC ATC ACC GTA GCA 1412
  88  A   T   P   L   L   V   I   F   S   P   I   L   V   P   A   L   I   T   V   A  107
1413 CTT CTC ATC ACT GGC TTT CTC TCC TCT GGT GGG TTT GCC ATT GCA GCT ATA ACC GTC TTC 1472
 108  L   L   I   T   G   F   L   S   S   G   G   F   A   I   A   A   I   T   V   F  127
1473 TCC TGG ATC TAT AAG TAC GCA ACG GGA GAG CAC CCA CAG GGG TCA GAT AAG TTG GAC AGT 1532
 128  S   W   I   Y   K   Y   A   T   G   E   H   P   Q   G   S   D   K   L   D   S  147
1533 GCA AGG ATG AAG CTG GGA ACC AAA GCT CAG GAT ATT AAA GAC AGA GCT CAA TAC TAC GGA 1592
 148  A   R   M   K   L   G   T   K   A   Q   D   I   K   D   R   A   Q   Y   Y   G  167
1593 CAG CAA CAT ACA GGT GGT GAG CAT GAC CGT GAC CGT ACT CGT GGT GGC CAG CAC ACT ACT 1652
 168  Q   Q   H   T   G   G   E   H   D   R   D   R   T   R   G   G   Q   H   T   T  187
1653 CTC GTT CCA CGA GGA TCC ATG GAT CCC AAC TGC TCC TGT GCC GCC AGT GAC TCC TGC ACC 1712
 188  L   V   P   R   G   S   M   D   P   N   C   S   C   A   A   S   D   S   C   T  207
```

FIGURE 8B

```
1713 TGC GCC GGC TCC TGC AAG TGC AAA GAG TGC AAA TGC ACC TCC TGC AAG AAA AGC TGC TGC 1772
 208  C   A   G   S   C   K   C   K   E   C   K   C   T   S   C   K   K   S   C   C   227

1773 TCC TGC TGT CCT GTG GGC TGT GCC AAG TGT GCC CAG GGC TGC ATC TGC AAA GGG GCG TCG 1832
 228  S   C   C   P   V   G   C   A   K   C   A   Q   G   C   I   C   K   G   A   S   247

1833 GAC AAG TGC AGC TGC TGT GCC TGA gcggccgcgagggctgcagaatgagttccaagatggtttgtgacgaag 1904
 248  D   K   C   S   C   C   A   *                                                    255

1905 ttagttggttgtttttatggaactttgtttaagcttgtaatgtggaaagaacgtgtggctttgtggttttaaatgttgg 1984

1985 tgaataaagatgtttcctttggattaactagtattttcctattggtttcatggttttagcacacaacattttaaatatg 2064

2065 ctgttagatgatatgctgcctgctttattatttacttacccctcaccttcagtttcaaagttgttgcaatgactctgtgt 2144

2145 agtttaagatcgagtgaaagtagattttgtctatatttattaggggtatttgatatgctaatggtaaacatggtttatga 2224

2225 cagcgtacttttttggttatggtgttgacgtttccttttaaacattatagtagcgtccttggtctgtgttcattggttga 2304

2305 acaaaggcacactcacttggagatgccgtctccactgatatttgaacaaagaattcggtacc             2366
```

FIGURE 11
A
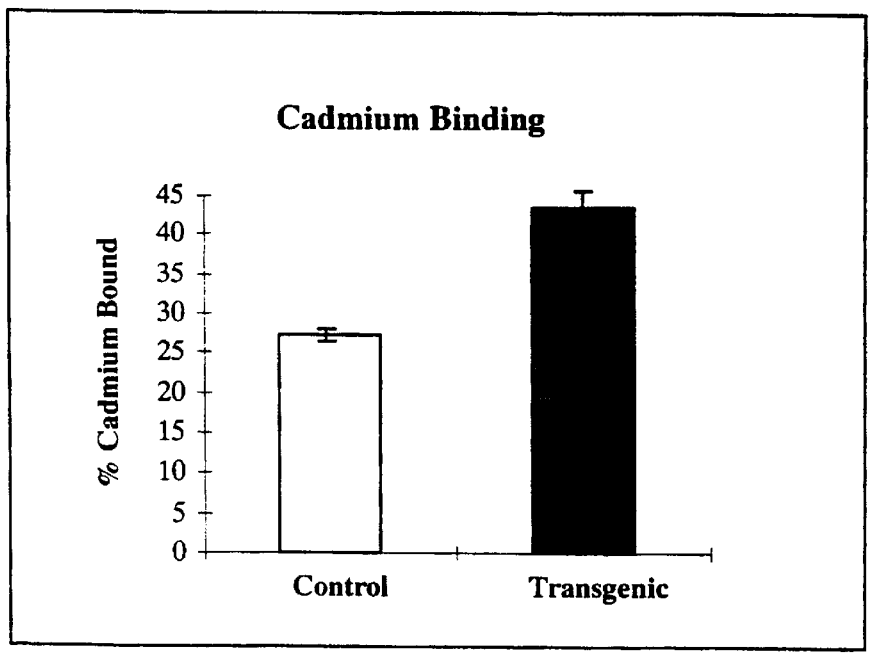
B
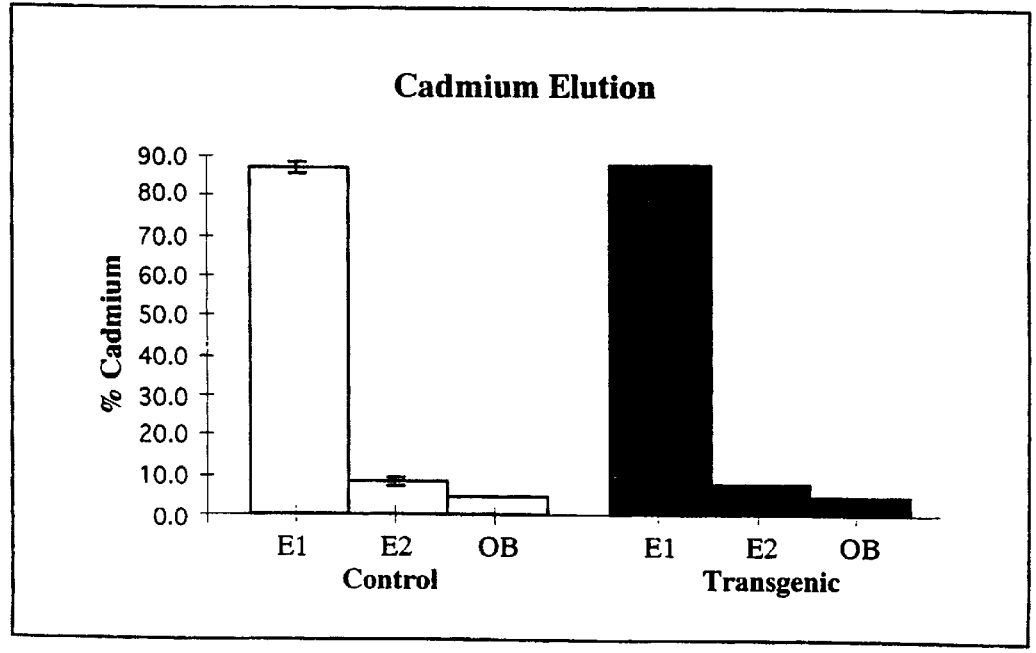

FIGURE 13

```
        NcoI
   1 CTCC ATG GAT CAA CGC AAT GGT TTT ATC CAA AGC CTT AAA GAT GAT CCA AGC CAA AGT GCT  61
   1       M   D   Q   R   N   G   F   I   Q   S   L   K   D   D   P   S   Q   S   A   19

62 AAC GTT TTA GGT GAA GCT CAA AAA CTT AAT GAC TCT CAA GCT CCA AAA GCT GAT GCG CAA  121
  20  N   V   L   G   E   A   Q   K   L   N   D   S   Q   A   P   K   A   D   A   Q    39

122 CAA AAT AAC TTC AAC AAA GAT CAA CAA AGC GCC TTC TAT GAA ATC TTG AAC ATG CCT AAC  181
  40  Q   N   N   F   N   K   D   Q   Q   S   A   F   Y   E   I   L   N   M   P   N    59

182 TTA AAC GAA GCG CAA CGT AAC GGC TTC ATT CAA AGT CTT AAA GAC GAC CCA AGC CAA AGC  241
  60  L   N   E   A   Q   R   N   G   F   I   Q   S   L   K   D   D   P   S   Q   S    79

242 ACT AAC GTT TTA GGT GAA GCT AAA AAA TTA AAC GAA TCT CAA GCA CCG AAA GCT GAT AAC  301
  80  T   N   V   L   G   E   A   K   K   L   N   E   S   Q   A   P   K   A   D   N    99

302 AAT TTC AAC AAA GAA CAA CAA AAT GCT TTC TAT GAA ATC TTG AAT ATG CCT AAC TTA AAC  361
 100  N   F   N   K   E   Q   Q   N   A   F   Y   E   I   L   N   M   P   N   L   N   119

362 GAA GAA CAA CGC AAT GGT TTC ATC CAA AGC TTA AAA GAT GAC CCA AGC CAA AGT GCT AAC  421
 120  E   E   Q   R   N   G   F   I   Q   S   L   K   D   D   P   S   Q   S   A   N   139

422 CTA TTG TCA GAA GCT AAA AAG TTA AAT GAA TCT CAA GCA CCG AAA GCG GAT AAC AAA TTC  481
 140  L   L   S   E   A   K   K   L   N   E   S   Q   A   P   K   A   D   N   K   F   159

482 AAC AAA GAA CAA CAA AAT GCT TTC TAT GAA ATC TTA CAT TTA CCT AAC TTA AAC GAA GAA  541
 160  N   K   E   Q   Q   N   A   F   Y   E   I   L   H   L   P   N   L   N   E   E   179

542 CAA CGC AAT GGT TTC ATC CAA AGC CTA AAA GAT GAC CCA AGC CAA AGC GCT AAC CTT TTA  601
 180  Q   R   N   G   F   I   Q   S   L   K   D   D   P   S   Q   S   A   N   L   L   199

602 GCA GAA GCT AAA AAG CTA AAT GAT GCT CAA GCA CCA AAA GCT GAC AAC AAA TTC AAC AAA  661
 200  A   E   A   K   K   L   N   D   A   Q   A   P   K   A   D   N   K   F   N   K   219

662 GAA CAA CAA AAT GCT TTC TAT GAA ATT TTA CAT TTA CCT AAC TTA ACT GAA GAA CAA CGT  721
 220  E   Q   Q   N   A   F   Y   E   I   L   H   L   P   N   L   T   E   E   Q   R   239

722 AAC GGC TTC ATC CAA AGC CTT AAA GAC GAT CCG GGG AAT TCC CGG GGA TCC GTC GAC CTG  781
 240  N   G   F   I   Q   S   L   K   D   D   P   G   N   S   R   G   S   V   D   L   259

782 CAG ATA ACA AAT TAG AAGCTTGC                                                      804
 260  Q   I   T   N   *    HindIII                                                     264
```

FIGURE 14A

```
   1 ccatggctatacccaacctcggtcttggtcacaccaggaactctctggtaagctagctccactccccagaaacaaccggc  80

81 gccaaattgccggaattgctgacctgaagacggaacatcatcgtcgggtccttgggcgattgcggcggaagatgggtcag 160

161 cttgggcttgaggacgagacccgaatcgagtctgttgaaaggttgttcattgggatttgtatacggagattggtcgtcga 240

241 gaggtttgagggaaaggacaaatgggtttggctctggagaaagagagtgcggctttagagagagaattgagaggtttaga 320

321 gagagatgcggcggcgatgacgggaggagagacgacgaggacctgcattatcaaagcagtgacgtggtgaaatttggaac 400

401 ttttaagaggcagatagatttattatttgtatccattttcttcattgttctagaatgtcgcggaacaaattttaaaacta 480

481 aatcctaaatttttctaattttgttgccaatagtggatatgtgggccgtatagaaggaatctattgaaggcccaaaccca 560

561 tactgacgagcccaaaggttcgttttgcgttttatgtttcggttcgatgccaacgccacattctgagctaggcaaaaaac 640

641 aaacgtgtctttgaatagactcctctcgttaacacatgcagcggctgcatggtgacgccattaacacgtggcctacaatt 720

721 gcatgatgtctccattgacacgtgacttctcgtctcctttcttaatatatctaacaaacactcctacctcttccaaaata 800

801 tatacacatcttttgatcaatctctcattcaaaatctcattctctctagtaaacaagaacaaaaaa ATG GCG GAT    876
   1                                                                    M   A   D    3

877 ACA GCT AGA GGA ACC CAT CAC GAT ATC ATC GGC AGA GAC CAG TAC CCG ATG ATG GGC CGA   936
   4  T   A   R   G   T   H   H   D   I   I   G   R   D   Q   Y   P   M   M   G   R   23

937 GAC CGA GAC CAG TAC CAG ATG TCC GGA CGA GGA TCT GAC TAC TCC AAG TCT AGG CAG ATT   996
  24  D   R   D   Q   Y   Q   M   S   G   R   G   S   D   Y   S   K   S   R   Q   I   43

997 GCT AAA GCT GCA ACT GCT GTC ACA GCT GGT GGT TCC CTC CTT GTT CTC TCC AGC CTT ACC  1056
  44  A   K   A   A   T   A   V   T   A   G   G   S   L   L   V   L   S   S   L   T   63

1057 CTT GTT GGA ACT GTC ATA GCT TTG ACT GTT GCA ACA CCT CTG CTC GTT ATC TTC AGC CCA  1116
  64  L   V   G   T   V   I   A   L   T   V   A   T   P   L   L   V   I   F   S   P   83

1117 ATC CTT GTC CCG GCT CTC ATC ACA GTT GCA CTC CTC ATC ACC GGT TTT CTT TCC TCT GGA  1176
  84  I   L   V   P   A   L   I   T   V   A   L   L   I   T   G   F   L   S   S   G  103

1177 GGG TTT GGC ATT GCC GCT ATA ACC GTT TTC TCT TGG ATT TAC AA gtaagcacacatttatcatct  1241
 104  G   F   G   I   A   A   I   T   V   F   S   W   I   Y   K                       118

1242 tacttcataatttgtgcaatatgtgcatgcatgtgttgagccagtagctttggatcaattttttttggtcgaataacaaa 1321

1322 tgtaacaataagaaattgcaaattctagggaacatttggttaactaaatacgaaatttgacctagctagcttgaatgtgt 1401

1402 ctgtgtatatcatctatataggtaaaatgcttggtatgatacctattgattgtgaatag G TAC GCA ACG GGA    1473
 119                                                              Y   A   T   G      122

1474 GAG CAC CCA CAG GGA TCA GAC AAG TTG GAC AGT GCA AGG ATG AAG TTG GGA AGC AAA GCT  1533
 123  E   H   P   Q   G   S   D   K   L   D   S   A   R   M   K   L   G   S   K   A  142
```

FIGURE 14B

```
1534 CAG GAT CTG AAA GAC AGA GCT CAG TAC TAC GGA CAG CAA CAT ACT GGT GGG GAA CAT GAC 1593
143  Q   D   L   K   D   R   A   Q   Y   Y   G   Q   Q   H   T   G   G   E   H   D   162

1594 CGT GAC CGT ACT CGT GGT GGC CAG CAC ACT ACT CTC GTT CCA CGA GGA TCC ATG GAT CAA 1653
163  R   D   R   T   R   G   G   Q   H   T   T   L   V   P   R   G   S   M   D   Q   182

1654 CGC AAT GGT TTT ATC CAA AGC CTT AAA GAT GAT CCA AGC CAA AGT GCT AAC GTT TTA GGT 1713
183  R   N   G   F   I   Q   S   L   K   D   D   P   S   Q   S   A   N   V   L   G   202

1714 GAA GCT CAA AAA CTT AAT GAC TCT CAA GCT CCA AAA GCT GAT GCG CAA CAA AAT AAC TTC 1773
203  E   A   Q   K   L   N   D   S   Q   A   P   K   A   D   A   Q   Q   N   N   F   222

1774 AAC AAA GAT CAA CAA AGC GCC TTC TAT GAA ATC TTG AAC ATG CCT AAC TTA AAC GAA GCG 1833
223  N   K   D   Q   Q   S   A   F   Y   E   I   L   N   M   P   N   L   N   E   A   242

1834 CAA CGT AAC GGC TTC ATT CAA AGT CTT AAA GAC GAC CCA AGC CAA AGC ACT AAC GTT TTA 1893
243  Q   R   N   G   F   I   Q   S   L   K   D   D   P   S   Q   S   T   N   V   L   262

1894 GGT GAA GCT AAA AAA TTA AAC GAA TCT CAA GCA CCG AAA GCT GAT AAC AAT TTC AAC AAA 1953
263  G   E   A   K   K   L   N   E   S   Q   A   P   K   A   D   N   N   F   N   K   282

1954 GAA CAA CAA AAT GCT TTC TAT GAA ATC TTG AAT ATG CCT AAC TTA AAC GAA GAA CAA CGC 2013
283  E   Q   Q   N   A   F   Y   E   I   L   N   M   P   N   L   N   E   E   Q   R   302

2014 AAT GGT TTC ATC CAA AGC TTA AAA GAT GAC CCA AGC CAA AGT GCT AAC CTA TTG TCA GAA 2073
303  N   G   F   I   Q   S   L   K   D   D   P   S   Q   S   A   N   L   L   S   E   322

2074 GCT AAA AAG TTA AAT GAA TCT CAA GCA CCG AAA GCG GAT AAC AAA TTC AAC AAA GAA CAA 2133
323  A   K   K   L   N   E   S   Q   A   P   K   A   D   N   K   F   N   K   E   Q   342

2134 CAA AAT GCT TTC TAT GAA ATC TTA CAT TTA CCT AAC TTA AAC GAA GAA CAA CGC AAT GGT 2193
343  Q   N   A   F   Y   E   I   L   H   L   P   N   L   N   E   E   Q   R   N   G   362

2194 TTC ATC CAA AGC CTA AAA GAT GAC CCA AGC CAA AGC GCT AAC CTT TTA GCA GAA GCT AAA 2253
363  F   I   Q   S   L   K   D   D   P   S   Q   S   A   N   L   L   A   E   A   K   382

2254 AAG CTA AAT GAT GCT CAA GCA CCA AAA GCT GAC AAC AAA TTC AAC AAA GAA CAA CAA AAT 2313
383  K   L   N   D   A   Q   A   P   K   A   D   N   K   F   N   K   E   Q   Q   N   402

2314 GCT TTC TAT GAA ATT TTA CAT TTA CCT AAC TTA ACT GAA GAA CAA CGT AAC GGC TTC ATC 2373
403  A   F   Y   E   I   L   H   L   P   N   L   T   E   E   Q   R   N   G   F   I   422

2374 CAA AGC CTT AAA GAC GAT CCG GGG AAT TCC CGG GGA TCC GTC GAC CTG CAG ATA ACA AAT 2433
423  Q   S   L   K   D   D   P   G   N   S   R   G   S   V   D   L   Q   I   T   N   442

2434 TAG aagcttgcatgcctgcaggtcgatcgttcaaacatttggcaataaagtttcttaagattgaatcctgttgccggtc 2512
443  *                                                                               443
2513 ttgcgatgattatcatataatttctgttgaattacgttaagcatgtaataattaacatgtaatgcatgacgttatttatg 2592

2593 agatgggttttatgattagagtcccgcaattatacatttaatacgcgatagaaaacaaaatatagcgcgcaaactagga 2672

2673 taaattatcgcgcgcggtgtcatctatgttactagat
```

OIL BODIES AND ASSOCIATED PROTEINS AS AFFINITY MATRICES

This application is a national phase entry under 35 USC 371 of PCT/CA97/00951 filed Dec. 5, 1997 which is a continuation-in-part of U.S. Ser. No. 08/767,026, filed Dec. 16, 1996 now U.S. Pat. No. 5,856,452, which is incorporated herein by reference.

FIELD OF THE INVENTION

This invention relates to the use of oil bodies and their associated proteins as affinity matrices for the separation and purification of target molecules from samples.

BACKGROUND OF THE INVENTION

Within the general field of biotechnology, the ability to effectively separate and purify molecules from complex sources, such as living cells, blood serum, or fermentation broth, is of critical importance. Applications in industry and research laboratories (where, for example, purified or partly purified proteins are used) are numerous and well documented in prior literature. See, for example, R. Meadon and G. Walsh in *Biotechnological Advances* 1994, 12: pp 635–646.

The majority of currently employed techniques for the separation of molecules capitalizes on the innate physical and chemical properties of the molecule of interest. Affinity-based purification technologies are unique in that they exploit the highly specific biological recognition between two molecular species which form an affinity pair. Binding of the two entities of the affinity pair occurs in almost all instances as a result of relatively weak chemical interactions, known as non-covalent bonds. Some art-recognized and commonly used affinity pairs include antibodies and their binding antigenic substances, nucleic acid binding proteins and nucleic acids, lipid binding proteins and lipids, lectins and carbohydrates, streptavidin/biotin complexes, protein A/immunoglobulin G complexes, and receptors and their binding molecules.

In general, affinity-based purification processes require that one member of the affinity pair is immobilized on a solid substrate or matrix that is insoluble in the fluid in which the other member of the pair resides. The molecular species of the affinity pair bound to the matrix is generally referred to as the ligand, while the liquid soluble member is generally referred to as the target member. However, it is important to note that these definitions do not impose any restrictions in a strict chemical sense. The vast majority of current ligand immobilization techniques rely on physical or chemical approaches. Physical ligand immobilization involves adsorption or entrapment of the ligand to a suitable support, while the chemical mode of immobilization is characterized by the formation of strong crosslinks or covalent attachments between the ligand and the matrix. It is a requirement that immobilization is accomplished in such a fashion that the capacity of the members of the affinity pair to recognize each other is not adversely affected by the immobilization procedure.

It is a disadvantage of the currently available physical and chemical techniques for immobilizing ligands that production processes are frequently time consuming and expensive. This is mainly due to the fact that immobilization techniques require the separate production of matrix material and ligands, which in a subsequent step must be coupled. An alternative mode of immobilizing proteins is described in U.S. Pat. No. 5,474,925 which documents a biological production system for the immobilization of enzymes in the fibre of cotton plants. This patent discloses what is believed to be the first biologically produced enzyme immobilization system and allows a one step production of matrix and ligand.

Subsequent to immobilization of the ligand on the matrix, a variety of affinity based purification techniques may be employed to accomplish selective binding between the affinity immobilized ligand and the target member. Affinity based purification techniques known in the prior art include perfusion affinity chromatography, affinity repulsion chromatography, hyperdiffusion affinity chromatography, affinity precipitation, membrane affinity partitioning, affinity cross-flow ultrafiltration and affinity precipitation. In the most widely used affinity based purification technique, affinity chromatography, a matrix containing a ligand is coated to, or packed on, the inside of a chromatographic column. A complex mixture containing the target member is then applied to the chromatographic column. Ideally, only the target molecules that specifically recognize the ligand bind in a non-covalent fashion to the chromatographic column, while all other molecular species present in the sample pass through the column.

In affinity partitioning, two solutions of substantially different densities are employed. The complex solution containing the target member is mixed with a solution of a different density containing the affinity ligand. Subsequent to mixing, the solutions are left to settle in order to permit the formation of two separate phases. Molecules tend to partition differentially between phases depending on their size, charge and specific interactions with the phase-forming solutions. Ligand-bound target protein selectively partitions to the phase containing the affinity ligand. For example, Coughlin and Baclaski in *Biotechnology Progress*, 1990 6: 307–309 reported the use of the biotin containing organic solution isooctane to transfer avidin from an aqueous solution to the isooctane solution. However, so far applications of affinity partitioning have been limited mainly due to the current lack of availability of suitable affinity matrix substances which can be employed in specific partitioning in two phase systems.

An important factor for the commercial development of biotechnology is the purification of bioproducts, which typically accounts for 50% or more of the total costs (Labrou, N. and Clonis, Y. D. in the *Journal of Biotechnology* 36: 95–119 (1994)). Many protein purification steps rely on column type separation procedures. In particular, large scale high-separation techniques such as column chromatography or batch-type based protein purification techniques are costly. In addition, crude material is less suitable for either column chromatography or batch separations, as contaminants may foul up sedimented resins and plug columns. Thus, affinity matrices are often only employed in a later stage of purification processes where substantial purity is critical, where the proteins are present in extremely dilute concentrations, or where high value proteins are required, for example in diagnostic and therapeutic proteins. These and other topics related to the use of affinity technology in biotechnological processes have been reviewed by Labrou, N. and Clonis, Y. D. in the *Journal of Biotechnology* 36: 95–119 (1994).

There is a need in the art to develop novel and economical methods for separating and purifying biological products from complex mixtures. The present inventors have found that subcellular oil storage structures, known as oil bodies, and their associated proteins are useful in this regard.

SUMMARY OF THE INVENTION

The present invention relates to a novel versatile biological system for the production of affinity matrices. The present inventors have found that oil bodies and their associated proteins can be used as affinity matrices for the separation of a wide variety of target molecules such as proteins, carbohydrates, lipids, organic molecules, nucleic acids, metals, cells and cell fractions from a sample.

In accordance with the invention, there is provided a method for the separation of a target molecule from a sample comprising: 1) contacting (i) oil bodies that can associate, either directly or indirectly, with the target molecule with (ii) a sample containing the target molecule; and 2) separating the oil bodies associated with the target molecule from the sample. The oil bodies and the sample containing the target molecule are brought into contact in a manner sufficient to allow the oil bodies to associate with the target. Preferably, oil bodies are mixed with the target. If desired, the target molecule may be further separated from the oil bodies.

In one aspect, the target molecule has affinity for, or binds directly to, the oil bodies or oil body protein. Examples of such targets include antibodies or other proteins that bind to oil bodies.

In another aspect, a ligand molecule may be used to associate the target molecule with the oil bodies.

In one embodiment, the ligand has natural affinity for the oil bodies or oil body protein. In a specific embodiment, the ligand is an antibody that binds the oil body protein. Such an antibody can be used to separate targets having affinity for the ligand antibody such as anti-IgG antibodies or protein A. A bivalent antibody may also be prepared having binding specificities for both the oil body protein and the target. The antibody against the oil body protein may also be fused to a second ligand having affinity for the target.

In another embodiment, the ligand is covalently attached to the oil bodies or oil body protein. In one embodiment, the ligand is a protein that is chemically conjugated or produced as a fusion protein with the oil body protein (as described in WO 96/21029). In the latter case, the fusion protein is targeted to and expressed on the oil bodies. In one example, the ligand fused to the oil body protein may be hirudin and can be used to purify thrombin. In another example, the ligand fused to the oil body protein may be metallothionein and can be used to separate cadmium from a sample. In a further example, the ligand fused to the oil body protein may be protein A and can be used to separate immunoglobulins. In yet another example, the ligand fused to the oil body protein may be cellulose binding protein and can be used to separate cellulose from a sample.

In another embodiment, the ligand may be covalently attached to the oil bodies. For example, the ligand may be a small organic molecule such as biotin. Biotinylated oil bodies can be used to separate avidin from a sample.

The present invention also includes modified oil bodies for use as an affinity matrix. Accordingly, the present invention includes a composition comprising oil bodies associated with a molecule, such as a ligand molecule or a target molecule. In one embodiment, the composition comprises oil bodies covalently attached to a ligand molecule, such as biotin.

The present invention also includes an affinity matrix for use in separating a target molecule from a sample, comprising oil bodies that can associate with the target molecule. The affinity matrix may additionally include a ligand molecule associated with the oil bodies, wherein the ligand molecule is capable of associating with the target molecule.

Other objects, features and advantages of the present invention will become apparent from the following detailed description and attached drawings. It should be understood, however, that the detailed description and associated examples are given by way of illustration only, and various changes and modifications thereto falling within the scope of the invention will become apparent to those skilled in the art. In addition, reference is made herein to various publications, patents and patent applications which are hereby incorporated by reference in their entirety.

BRIEF DESCRIPTION OF THE DRAWINGS

FIG. 1. The nucleotide and deduced amino acid sequence of the 18 KDa oleosin from *Arabidopsis thaliana* as shown in SEQ ID NO:1 and SEQ ID NO:2.

FIGS. 2A and 2B. Sequence of an Arabidopsis oleosin-hirudin fusion. Indicated are a portion of the oleosin genomic sequence (from base 1–1620 as reported in van Rooijen et al 1992, *Plant Mol. Biol.* 18: 1177–1179), a spacer sequence (base 1621–1635, underlined) and the synthetic DNA sequence encoding the mature hirudin variant-2 isoform (base 1636–1833, italicized) This gene fusion is regulated by the 5' upstream region of the Arabidopsis oleosin (bases 1–861) and the nopaline synthase termination sequence (base 1855–2109). The sequence is also shown in SEQ ID NO:3 and SEQ ID NO:4.

FIG. 3. Outline of the steps employed in the construction of pCGOBHIRT, containing the entire oleosin-hirudin construct.

FIGS. 8A and 8B. Sequence of an oleosin metallothionein fusion. Indicated are the coding sequence of a *B. napus* oleosin cDNA (bases 1092–1652, van Rooijen, 1993, *Ph.D. Thesis*, University of Calgary), a spacer sequence (bases 1653–1670, underlined) and the human metallothionein gene mt-II (bases 1671–1876, Varshney and Gedamu, 1984, *Gene*, 31: 135–145)). The gene fusion is regulated by an Arabidopsis oleosin promoter (bases 1–1072) and ubiquitin termination sequence (bases 1870–2361, ubi3'; Kawalleck et al., 1993, *Plant Mol. Biol.* 21: 673–684). The sequence is also shown in SEQ ID NO:6 and SEQ ID NO:7.

FIG. 11. Illustrates the binding (A) and elution (B) of cadmium to an oil body matrix from wildtype *B. carinata* seeds and *B. carinata* seeds transformed with a construct expressing oleosin metallothionein gene fusion. Shown is the percentage cadmium bound to the oil body fraction of an oil body fraction harvested from transgenic and untransformed seeds. Bars represent average values of 5 replicate experiments (binding) and 3 replicates (elution).

FIG. 13. Oligonucleotide primers used to amplify the sequence of the *S. aureus* protein A (The sequence is also shown in SEQ ID NO:8; The protein sequence is also shown in SEQ ID NO:9). Primer BK266, 5'C TCC ATG GAT CAA CGC AAT GGT TTA TC 3' (SEQ ID NO:10), a NcoI site (italicized) and a sequence identical to a portion of the protein A gene as contained within vector pRITZ2T (Pharmacia) (underlined) are indicated. Primer BK267, 5' GC AAG CTT CTA ATT TGT TAT CTG CAG GTC 3' (SEQ ID NO:11), a HindIII site (italicized), a stop codon (bold) and a sequence complementary to a portion of the protein A gene as contained within pRIT2T (Pharmacia) (underlined) are indicated. The PCR product was digested with NcoI and HindIII and ligated into pCGNOBPGUSA (Van Rooijen and Moloney, 1995, *Plant Physiol.* 109: 1353–1361) from which the NcoI-GUS-HindIII fragment had been removed.

FIGS. 14A and 14B. Sequence of an Arabidopsis oleosin-protein A fusion (The sequence is also shown in SEQ ID NO:12 and the protein sequence is also shown in SEQ ID NO:13 and 14). Indicated are a portion of the oleosin genomic sequence (from base 1–1626, as reported in van Rooijen et al., 1992 *Plant Mol. Biol.* 18: 1177–1179), a spacer sequence encoding a thrombin cleavage site (base 1627–1647, underlined) and the DNA sequence encoding protein A (base 1648–2437, italicized). Expression is regulated by the Aralidopsis 5' upstream region of the Arabidopsis oleosin (base 1–867) and the nopaline synthase terminator region (base 2437–2700).

DETAILED DESCRIPTION OF THE INVENTION

Figure 4:
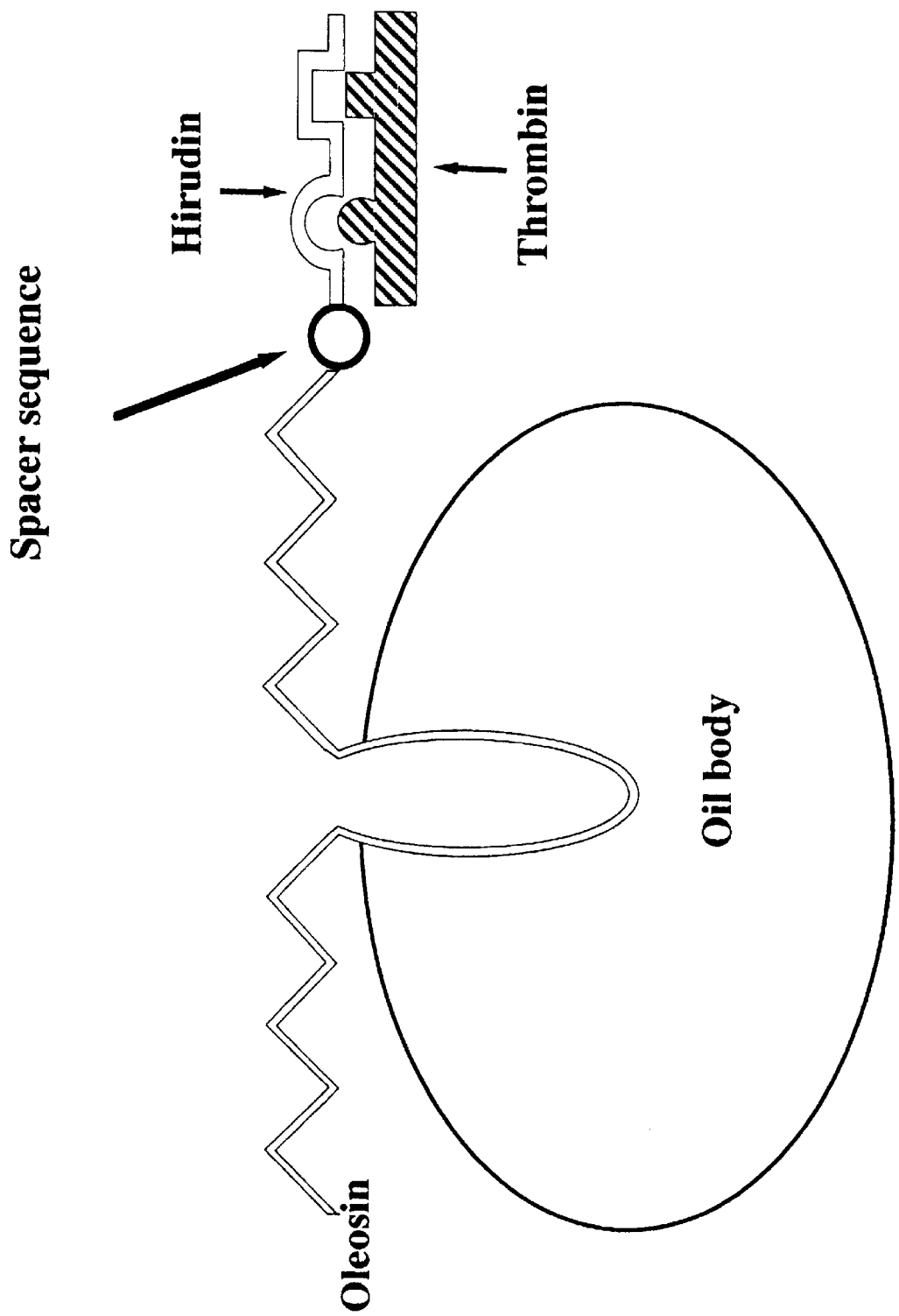
FIG. 4. Schematic diagram illustrating the configuration of the oleosin-hirudin fusion protein on the oil body and the binding of thrombin.

As hereinbefore mentioned, the present invention relates to a novel biological affinity matrix system that employs oil bodies and their associated proteins. The affinity matrix is suitable for the highly-efficient separation of specific targets, including proteins, carbohydrates, lipids, nucleic acids, cells and subcellular organelles, metals and ions, from a sample.

The present invention provides a method for the separation of a target molecule from a sample comprising: 1) contacting (i) oil bodies that can associate either directly or indirectly with the target molecule with (ii) a sample containing the target molecule; and 2) separating the oil bodies associated with the target molecule from the sample. The oil bodies and the sample containing the target molecule are brought into contact in a manner sufficient to allow the oil bodies to associate with the target. Preferably, the oil bodies are mixed with the target. Indirect association of the oil bodies with the target can be effected using a ligand molecule that can associate with both the oil bodies and the target molecule. The ligand therefore serves to bridge or join the oil bodies with the target molecule. If desired, the target molecule may be further separated from the oil bodies and the ligand, if present.

Each of the components of the affinity matrix are discussed in turn below.

Targets

The term "target" as used herein denotes a desired molecule that one wants to purify, isolate or separate from a sample such as a biological mixture. This technology is amenable for use with virtually any target for which a ligand can be obtained or any target that can directly associate with or bind to an oil body or oil body protein. Possible ligand/target pairs include but are not limited to: protein subunit/subunit associations, antibodies/antigens, receptor protein/signal molecules, nucleic acid binding proteins/nucleic acids; lectins/carbohydrates; lipid binding proteins/lipids; ion binding proteins/ions; and ligands to surface epitopes/cells or subcellular organelles. The target may be obtained from any natural source or may be synthesized chemically. If the target is a macromolecule such as a protein or nucleic acid it may also be produced in recombinant form using any suitable expression system such as bacteria, yeast, plant, insect, mammalian, etc.

Ligands

The term "ligand" used herein denotes a molecule that is capable of associating with both the target molecule and the oil bodies or oil body protein (discussed below). The term "associating with" as used herein includes both covalent and non-covalent binding of the ligand to the oil bodies or the target molecule. For example, the ligand molecule may be covalently attached to the oil bodies and non-covalently associate with the target (and vice-versa), or the ligand may non-covalently associate with both the oil bodies and the target molecule. The ligand may be any molecule that can bridge the oil bodies or oil body protein and the target molecule and can include a protein, nucleic acid, carbohydrate or small organic molecule. The ligand may be comprised of two molecules, a first molecule that associates with the oil bodies and a second molecule that associates with the target, wherein the first molecule and the second molecule associate with each other.

The affinity ligand proteins used for this methodology may be derived from naturally-occurring, known ligand pairs such as those listed above. Alternatively, the ligand may be obtained by screening proteins extracted from cells or organisms, synthesized chemically or produced in libraries comprised of combinatorial peptide sequences, antibodies, or expressed DNA sequences.

In one embodiment, the ligand has natural affinity for the oil bodies or the oil body protein. For example, the ligand may be a protein such as an antibody, that has affinity for the oil body protein. The ligand may also be a molecule other than a protein which has natural affinity for the oil body or oil body protein. Such ligands, capable of binding to the oil bodies or oil body protein, may be associated with a second molecule that can bind the target molecule. For example, the ligand molecule may be an antibody conjugated to avidin and can be used to purify biotin from a sample.

In another embodiment, the ligand is covalently linked to the oil bodies or oil body protein by chemical or recombinant means. Chemical means for preparing fusions or conjugates are known in the art and can be used to prepare a ligand-oil body protein fusion. The method used to conjugate the ligand and oil body must be capable of joining the ligand with the oil body protein without interfering with the ability of the ligand to bind to the target molecule. In one example, the ligand may be a small organic molecule such as biotin that is covalently attached to the oil bodies. Biotinylated oil bodies can be used to separate avidin from a sample. The present invention also includes modified oil bodies such as biotinylated oil bodies for use as an affinity matrix. Accordingly, the present invention includes a composition comprising oil bodies attached to a molecule, such as a ligand or a target molecule.

In a preferred embodiment, the ligand is a protein and can be conjugated to the oil body protein using techniques well known in the art. There are several hundred crosslinkers available that can conjugate two proteins. (See for example "Chemistry of Protein Conjugation and Crosslinking". 1991, Shans Wong, CRC Press, Ann Arbor). The crosslinker is generally chosen based on the reactive functional groups available or inserted on the ligand. In addition, if there are no reactive groups a photoactivatible crosslinker can be used. In certain instances, it may be desirable to include a spacer between the ligand and the oil-body protein. Crosslinking agents known to the art include the homobifunctional agents: glutaraldehyde, dimethyladipimidate and Bis(diazobenzidine) and the heterobifunctional agents: m-Maleimidobenzoyl-N-Hydroxysuccinimide and Sulfo-m-Maleimidobenzoyl-N-Hydroxysuccinimide.

A ligand protein-oil body protein fusion may also be prepared using recombinant DNA techniques. In such a case a DNA sequence encoding the ligand is fused to a DNA sequence encoding the oil body protein, resulting in a chimeric DNA molecule that expresses a ligand-oil body protein fusion protein (discussed in greater detail below). In order to prepare a recombinant fusion protein, the sequence of the DNA encoding the ligand must be known or be obtainable. By obtainable it is meant that a DNA sequence sufficient to encode the protein ligand may be deduced from the known amino acid sequence. It is not necessary that the entire gene sequence of the ligand be used provided that a subsequence encoding the binding domain of the protein ligand is known. Therefore, the ligand can include the complete sequence of, or the binding domain from, the specific ligand protein in question.

If the DNA sequence of the desired ligand is known, the gene may be synthesized chemically using an oligonucleotide synthesizer. Alternatively, the clone carrying the ligand gene may be obtained from either cDNA or genomic libraries containing the gene by probing with a labelled complementary DNA sequence. The gene may also be specifically amplified from the library using gene-specific oligonucleotide primers and the PCR. If the DNA sequence of the desired ligand is not known, then a partial amino acid sequence may be obtained through N-terminal sequencing of the protein (Matsudaira 1987; *J. Biol. Chem.* 262: 10035–10038). Labelled probes may be synthesized based upon the DNA sequences deduced from this amino acid sequence and used to screen cDNA or genomic libraries as described above. The clone carrying the gene may also be identified from a cDNA expression library by probing either with antibodies raised against the protein ligand, or with the target protein.

Ligands may also be uncovered by probing mixtures of proteins with the target. The target can be immobilized on a support matrix and used to screen proteins extracted from cells and tissues or synthesized chemically. Following binding between the ligand protein and the immobilized target, the matrix is separated from the solution and washed. The protein ligand is subsequently eluted from the matrix and the sequence determined as described above. Alternatively, recombinant protein libraries produced by phage display, such as those comprised of combinatorial peptide sequences (Smith, 1985; *Science* 228: 1315–1317) or antibody repertoires (Griffiths et al., 1994, *EMBO J.* 13: 3245–3260, Nissim et al., 1994, *EMBO J.* 13: 692–698) can be screened with the immobilized target. In this case, binding between the protein ligand and the target would enable separation and recovery of the phage expressing the ligand from the large, complex population of phage encoding non-binding proteins. A two-hybrid system such as that in yeast (Fields and Sternglanz, 1994; *Trends Genet.* 10: 286–292) might also be used to identify a ligand from an expressed cDNA library. Here, a gene fusion is constructed between the sequence encoding the target protein and that of a DNA binding protein. Cells containing this construct are transformed with constructs from a cDNA library where the sequences have been fused to that of a transcriptional activator. Binding between ligands derived from the cDNA library with the target protein allows transcription of a reporter gene to occur. Clones expressing the ligand are then recovered.

To specifically uncover a ligand to oil bodies, a complete or partial oleosin protein may be used as target in any of the above methods. Alternatively, it may be possible to employ intact oil bodies for screening protein extracts, synthetic peptides or phage display libraries. In this case, the oil body would serve both as target and immobilization matrix. Using this approach, a wider variety of ligands may be uncovered; that exhibit affinity not only to oleosins, but to other epitopes present on oil bodies.

Oil Bodies and Oil Body Proteins

Oil bodies are small, spherical, subcellular organelles encapsulating stored triacylglycerides, an energy reserve used by many plants. Although they are found in most plants and in different tissues, they are particularly abundant in the seeds of oilseeds where they range in size from under one micron to a few microns in diameter. Oil bodies are comprised of the triacylglycerides surrounded by a half-unit membrane of phospholipids and embedded with a unique type of protein known as an oil body protein. The term "oil body" or "oil bodies" as used herein includes any or all of the triacylglyceride, phospholipid or protein components present in the complete structure. The term "oil body protein" as used herein means a protein that is naturally present in an oil body. In plants, the predominant oil body proteins are termed "oleosins". Oleosins have been cloned and sequenced from many plant sources including corn, rapeseed, carrot and cotton. The oleosin protein appears to be comprised of three domains; the two ends of the protein, N- and C-termini, are largely hydrophilic and reside on the surface of the oil body exposed to the cytosol while the highly hydrophobic central core of the oleosin is firmly anchored within the membrane and triacylglyceride. Oleosins from different species represent a small family of proteins showing considerable amino acid sequence conservation, particularly in the central region of protein. Within an individual species, a small number of different isoforms may exist.

Oil bodies from individual species exhibit a roughly uniform size and density which is dependent in part upon the precise protein/phospholipid/triacylglyceride composition. As a result, they may be simply and rapidly separated from liquids of different densities in which they are suspended. For example, in aqueous media where the density is greater than that of the oil bodies, they will float under the influence of gravity or applied centrifugal force. In 95% ethanol where the density is less than that of the oil bodies, they will sediment under the same conditions. Oil bodies may also be separated from liquids and other solids present in solutions or suspensions by methods that fractionate on the basis of size. For example, the oil bodies from *B. napus* are minimal, approximately 0.51 μm in diameter, and thus may be separated from smaller components using a membrane filter with a pore size less than this diameter.

The oil bodies of the subject invention are preferably obtained from a seed plant and more preferably from the group of plant species comprising: thale cress (*Arabidopsis thaliana*), rapeseed (Brassica spp.), soybean (*Glycine max*), sunflower (*Helianthus annuus*), oil palm (*Elaeis guineeis*), cottonseed (Gossypium spp.), groundnut (*Arachis hypogaea*), coconut (*Cocus nucifera*), castor (*Ricinus communis*), safflower (*Carthamus tinctorius*), mustard (Brassica spp. and *Sinapis alba*), coriander (*Coriandrum sativum*) linseed/flax (*Linum usitatissimum*), and maize (*Zea mays*). Plants are grown and allowed to set seed using agricultural cultivation practises well known to a person skilled in the art. After harvesting the seed and removal of foreign material such as stones or seed hulls, for by example sieving, seeds are preferably dried and subsequently processed by mechanical pressing, grinding or crushing. The oil body fraction may be obtained from the crushed seed fraction by capitalization on separation techniques which exploit differences in density between the oil body fraction and the aqueous fraction, such as centrifugation, or using size exclusion-based separation techniques, such as membrane filtration, or a combination of both of these. Typically, seeds are thoroughly ground in five volumes of a cold aqueous buffer. A wide variety of buffer compositions may be employed, provided that they do not contain high concentrations of strong organic solvents such as acetone or diethyl ether, as these solvents may disrupt the oil bodies. The solution density of the grinding buffer may be increased with the addition of 0.4–0.6 M sucrose, in order to facilitate washing as described below. The grinding buffer will also typically contain 0.5 M NaCl to help remove soluble proteins that are not integrally bound to the oil body surface.

Following grinding, the homogenate is centrifuged resulting in a pellet of particulate and insoluble matter, an aqueous phase containing soluble components of the seed, and a surface layer comprised of oil bodies with their associated proteins. The oil body layer is skimmed from the surface and thoroughly resuspended in one volume of fresh grinding buffer. It is important that aggregates of oil bodies are dissociated as thoroughly as possible in order to ensure efficient removal of contaminants in the subsequent washing steps. The resuspended oil body preparation is layered under a floatation solution of lower density (e.g. water, aqueous buffer) and centrifuged, again, separating oil body and aqueous phases. This washing procedure is typically repeated at least three times, after which the oil bodies are deemed to be sufficiently free of contaminating soluble proteins as determined by gel electrophoresis. It is not necessary to remove all of the aqueous phase and to the final preparation water or 50 mM Tris-HCl pH 7.5 may be added and if so desired the pH may be lowered to pH 2 or raised to pH 10. Protocols for isolating oil bodies from oil seeds are available in Murphy, D. J. and Cummins I., 1989, Phytochemistry, 28: 2063–2069; and in: Jacks, T. J. et al., 1990, JAOCS, 67: 353–361. A preferred protocol is detailed in example 1 of the present specification.

Oil bodies other than those derived from plants may also be used in the present invention. A system functionally equivalent to plant oil bodies and oleosins has been described in bacteria (Pieper-Füirst et al., 1994, *J. Bacteriol.* 176: 4328), algae (Rossler, P. G., 1988, *J. Physiol.* (London), 24: 394–400) and fungi (Ting, J. T. et al., 1997, *J. Biol Chem.* 272: 3699–3706). Oil bodies from these organisms, as well as those that may be discovered in other living cells by a person skilled in the art, may also be employed according to the subject invention.

Affinity Matrices

As hereinbefore mentioned, the present invention provides a novel affinity matrix system for the purification of a target molecule from a sample. In one embodiment, the affinity matrix comprises oil bodies that can bind a target molecule in a sample. In such an embodiment, the target molecule may be an antibody that can bind an oil body protein. In another embodiment, the affinity matrix comprises oil bodies or oil body proteins and a ligand that is associated with the oil bodies or oil body proteins and has affinity for a target molecule. In such an embodiment, the ligand may be non-covalently or covalently attached to the oil bodies or oil body protein (as described above).

It is an advantage of the present invention that target substances can be purified or removed from samples through non-covalent association with oil bodies followed by oil body separation. A number of different oil body-ligand configurations are possible. Targets with inherent affinity for a specific ligand proteins such as hirudin to thrombin or heavy metals to metallothionein, may be purified or separated with oil bodies containing that ligand fused to an oleosin. Alternatively, a protein target may also be purified or separated with an oil body affinity matrix by fusing the target to an oil body-specific ligand or to a ligand complimentary to that fused to an oleosin. If desired, a protease recognition site or chemical cleavage site may be engineered between the ligand and the target protein to enable proteolytic removal of the ligand from the target protein in the course of purification. A multivalent ligand may also be constructed, such as a bivalent single-chain antibody, in which one domain of the ligand has an affinity for an oil body and the other domain(s) exhibits affinity for the target. In this case, neither the oil body nor the target molecule need to be covalently fused to a ligand. Also, concatamers of ligands may be used to increase the affinity of a matrix for a target, or the sequence of a ligand may be mutated to modulate the affinity for a target when such conditions are desirable. Further, mixtures of different ligands may be fused to recover/remove different types of targets simultaneously. Fusions between different ligands may also be constructed to form bridges between different types of targets or between targets and the oil body affinity matrix. Binding to the affinity matrix may also be achieved by forming bridges between ligand or ligand and target sequences, such as $Zn^{++}$ ions bridging between polyhistidine sequences.

There are several advantages associated with the use of oil body affinity matrices that make them attractive as purification tools. The flexibility in design that is possible through the different configurations described above, enables a matrix to be constructed to best meet the requirements for a specific target. Also, production of the matrix as part of a natural biological process in seeds is extremely cost-effective, since purification and immobilization of the ligand are not necessary. In the case of oleosin-ligand fusions, the ligand is immobilized on the oil body as a result of oleosin targeting within the cell, while oil body-specific ligands will naturally associate with the matrix while present in complex mixtures. Natural immobilization of the ligand on the matrix may also be advantageous in that it eliminates the requirement for chemical cross-linking that may compromise the affinity of the ligand for the target. Finally, oil body affinity matrices offer a unique and attractive purification option particularly for large scale operations. The ability to separate the matrix through floatation as a loose suspension enables it to be employed with crude material containing what might otherwise be prohibitive amounts of particulate contaminants. The presence of these contaminants will often foul and block conventional solid matrices applied in columns or batch suspensions limiting their use at early stages in the purification process.

As mentioned previously, in one embodiment of the invention, ligand protein sequences are genetically fused to the oil body protein. In order to prepare such genetic fusions, a chimeric DNA sequence is prepared that encodes an oil body protein-ligand fusion protein and consists of (a) a DNA sequence encoding a sufficient portion of an oil body protein to provide targeting of the fusion protein to the oil bodies and (b) a DNA sequence encoding a sufficient portion of the ligand protein to provide binding of the target. The inventors have determined that, in general, the N-terminus and the hydrophobic core of an oil body protein are sufficient to provide targeting of the fusion protein to the oil bodies. In particular, for oleosins derived from. the plant *Arabidopsis thaliana* amino acids 2 through 123 (as shown in SEQ ID NO:1) are sufficient in this regard.

The ligand may be fused to either the N- and/or C-terminal end of the oleosin. It may also be possible to construct an internal fusion between the ligand and oleosin or to fuse the ligand between two oleosin proteins. The chimeric DNA sequence encoding an oil body protein fused to a ligand may be transfected into a suitable vector and used to transform a plant. Two types of vectors are routinely employed. The first type of vector is used for the genetic-engineering and assembly of constructs and typically consists of a backbone such as found in the pUC family of vectors, enabling replication in easily-manipulated and maintained gram negative bacteria such as *E. coli*. The second type of vector typified by the Ti and Ri plasmids, specify DNA transfer functions and are used when it is desired that the constructs be introduced into the plant and stably integrated into its genome via Agrobacterium-mediated transformation.

A typical construct consists, in the 5' to 3' direction, of a regulatory region complete with a promoter capable of directing expression in plants (preferably seed-specific expression), a protein coding region, and a sequence containing a transcriptional termination signal functional in plants. The sequences comprising the construct may be either natural or synthetic or any combination thereof.

Both non-seed specific promoters, such as the 35-S CaMV promoter (Rothstein et al., 1987; *Gene* 53: 153–161) and seed-specific promoters such as the phaseolin promoter (Sengupta-Gopalan et al., 1985; PNAS USA 82: 3320–3324) or the Arabidopsis 18 kDa oleosin (Van Rooijen et al., 1992; Plant Mol. Biol. 18: 1177–1179) promoters may be used. In addition to the promoter, the regulatory region contains a ribosome binding site enabling translation of the transcripts in plants and may also contain one or more enhancer sequences, such as the AMV leader (Jobling and Gehrke 1987; Nature 325: 622–625), to increase the expression of product.

The coding region of the construct will typically be comprised of sequences encoding a ligand fused in frame to an oleosin and ending with a translational termination codon. The sequence for the oleosin may be comprised of any DNA sequence, or part thereof, natural or synthetic, sufficient to encode a protein that can be correctly targeted to, and stably expressed on, an oil body. A detailed description of the characteristics of such a sequence has been reported previously in Moloney, 1993; PCT Patent Appl. WO 93/21320 which is hereby incorporated by reference. The sequence may also include introns. The ligand-encoding region may in turn be comprised of any individual, or combination of, ligand sequences identified as described above. If desired, a protease or chemical recognition site may be engineered between the ligand and the target protein to enable proteolytic removal of the ligand from the target protein in the course of purification.

The region containing the transcriptional termination signal may comprise any such sequence functional in plants such as the nopaline synthase termination sequence and additionally may include enhancer sequences to increase the expression of product.

The various components of the construct are ligated together using conventional methods, typically into a pUC-based vector. This construct may then be introduced into an Agrobacterium vector and subsequently into host plants, using one of the transformation procedures outlined below.

A variety of techniques are available for the introduction of DNA into host cells. For example, the chimeric DNA constructs may be introduced into host cells obtained from dicotyledonous plants, such as tobacco, and oleaginous species, such as *B. napus* using standard Agrobacterium vectors; by a transformation protocol such as that described by Moloney et al., 1989, (*Plant Cell Rep.,* 8: 238–242) or Hinchee et al., 1988, (*Bio/Technol.,* 6: 915–922); or other techniques known to those skilled in the art. For example, the use of T-DNA for transformation of plant cells has received extensive study and is amply described in EPA Serial No. 120,516; Hoekema et al., 1985, (Chapter V, In: *The Binary Plant Vector System* Offset-drukkerij Kanters B. V., Alblasserdam); Knauf, et al., 1983, (*Genetic Analysis of Host Range Expression by Agrobacterium*, p. 245, In Molecular Genetics of the Bacteria-Plant Interaction, Puhler, A. ed., Springer-Verlag, NY); and An et al., 1985, (*EMBO J.,* 4: 277–284). Conveniently, explants may be cultivated with *A. tumefaciens* or *A. rhizogenes* to allow for transfer of the transcription construct to the plant cells. Following transformation using Agrobacterium the plant cells are dispersed in an appropriate medium for selection, subsequently callus, shoots and eventually plantlets are recovered. The Agrobacterium host will harbour a plasmid comprising the vir genes necessary for transfer of the T-DNA to the plant cells. For injection and electroporation, (see below) disarmed Ti-plasmids (lacking the tumour genes, particularly the T-DNA region) may be introduced into the plant cell.

The use of non-Agrobacterium techniques permits the use of the constructs described herein to obtain transformation and expression in a wide variety of monocotyledonous and dicotyledonous plants and other organisms. These techniques are especially useful for species that are intractable in an Agrobacterium transformation system. Other techniques for gene transfer include biolistics (Sanford, 1988, *Trends in Biotech.,* 6: 299–302), electroporation (Fromm et al., 1985, *Proc. Natl. Acad. Sci. USA,* 82: 5824–5828; Riggs and Bates, 1986, *Proc. Natl. Acad. Sci. USA* 83: 5602–5606) or PEG-mediated DNA uptake (Potrykus et al., 1985, *Mol. Gen. Genet.*, 199: 169–177).

In a specific application, such as to *B. napus*, the host cells targeted to receive recombinant DNA constructs typically will be derived from cotyledonary petioles as described by Moloney et al., (1989, *Plant Cell Rep.*, 8: 238–242). Other examples using commercial oil seeds include cotyledon transformation in soybean explants (Hinchee et al., 1988. *BiolTechnology*, 6: 915–922) and stem transformation of cotton (Umbeck et al., 1981, *Bio/Technology*, 5: 263–266).

Following transformation, the cells, for example as leaf discs, are grown in selective medium. Once shoots begin to emerge, they are excised and placed onto rooting medium. After sufficient roots have formed, the plants are transferred to soil. Putative transformed plants are then tested for presence of a marker. Southern blotting is performed on genomic DNA using an appropriate probe, for example an *A. thaliana* oleosin gene, to show that integration of the desired sequences into the host cell genome has occurred.

The expression cassette will normally be joined to a marker for selection in plant cells. Conveniently, the marker may be resistance to a herbicide, e.g. phosphinothricin or glyphosate, or more particularly an antibiotic, such as kanamycin, G418, bleomycin, hygromycin, chloramphenicol, or the like. The particular marker employed will be one which will allow for selection of transformed cells compared with cells lacking the introduced recombinant DNA.

The fusion peptide in the expression cassette constructed as described above, expresses at least preferentially in developing seeds. Accordingly, transformed plants grown in accordance with conventional ways, are allowed to set seed. See, for example, McCormick et al. (1986, *Plant Cell Reports*, 5: 81–84). Northern blotting can be carried out using an appropriate gene probe with RNA isolated from tissue in which transcription is expected to occur, such as a seed embryo. The size of the transcripts can then be compared with the predicted size for the fusion protein transcript.

Oil body proteins are then isolated from the seed and analyses performed to determine that the fusion peptide has been expressed. Analyses can be for example by SDS-PAGE. The fusion peptide can be detected using an antibody to the oleosin portion of the fusion peptide. The size of the fusion peptide obtained can then be compared with predicted size of the fusion protein.

Two or more generations of transgenic plants may be grown and either crossed or selfed to allow identification of plants and strains with desired phenotypic characteristics including production of recombinant proteins. It may be desirable to ensure homozygosity of the plants, strains or lines producing recombinant proteins to assure continued inheritance of the recombinant trait. Methods of selecting homozygous plants are well know to those skilled in the art of plant breeding and include recurrent selfing and selection and anther and microspore culture. Homozygous plants may also be obtained by transformation of haploid cells or tissues followed by regeneration of haploid plantlets subsequently converted to diploid plants by any number of known means, (e.g.: treatment with colchicine or other microtubule disrupting agents).

Method of Separating Target Molecules Using the Affinity Matrices

As hereinbefore mentioned, the present invention relates to a method of separating a target molecule from a sample using the above described oil body proteins and in some cases, ligands. In the method of the invention, oil bodies are mixed with a sample containing the desired target and the interaction between the ligand and target results in the non-covalent association of the target with the oil body. Following centrifugation, the oil bodies and affinity-bound target are separated from the aqueous phase, effectively purifying the target from any contaminants present in the original sample. Repeating the washing step ensures that any remaining contaminants are removed.

Following their attachment to oil bodies, targets may be eluted under conditions determined empirically for each individual ligand-target pair. Treatment of the bound matrix with the appropriate eluent and centrifugation enables recovery of the purified target in the aqueous phase. If the target is a ligand-protein fusion containing a protease recognition site, then it may be treated with the appropriate protease to remove the ligand. The free ligand may then be separated from the target protein by re-application of the oil body affinity matrix or through conventional protein purification methods.

The chemical and physical properties of the affinity matrix may be varied in at least two ways. Firstly, different plant species contain oil bodies with different oil compositions. For example, coconut is rich in lauric oils (C12), while erucic acid oils (C22) are abundantly present in some Brassica spp. Furthermore, proteins associated with the oil bodies will vary between species. Secondly, the relative amounts of oils may be modified within a particular plant species by applying breeding and genetic engineering techniques or a combination of these known to the skilled artisan. These techniques aim at altering the relative activities of enzymes controlling the metabolic pathways involved in oil synthesis. Through the application of these techniques, seeds with a sophisticated set of different oils are obtainable. For example, breeding efforts have resulted in the development of a rapeseed with a low erucic acid content (Canola) (Bestor, T. H., 1994, Dev. Genet. 15: 458) and plant lines with oils with alterations in the position and number of double bonds, variation in fatty acid chain length and the introduction of desirable functional groups have all been generated through genetic engineering (Töpfer et al., 1995, Science, 268: 681–685). Using similar approaches a person skilled in the art will be able to further expand on the presently available sources of oil bodies. Variant oil compositions will result in variant physical and chemical properties of the oil body fraction. Thus by selecting oilseeds or mixtures thereof from different species or plant lines as a source for oil bodies, a broad repertoire of oil body matrices with different textures and viscosities may be acquired.

Applications of Oil Body Affinity Matrices

Given that it is possible to engineer oil body affinity matrices for several classes of proteins, multiple uses for oil body based affinity matrices are envisioned. Bacteria, fungi, plants and animals all contain proteins which are able to specifically interact with agents such as ions, metals, nucleic acids, sugars, lipids and other proteins. These agents may be immobilized using oil body technology.

The oil body protein affinity matrices can be used to isolate any target molecule that can bind to the oil body protein, either directly or indirectly through a ligand molecule. Examples of target molecules that may be isolated from a sample using the methodology of the present invention include proteins, peptides, organic molecules, lipids, carbohydrates, nucleic acids, cells, cell fragments, viruses and metals. In particular, the inventors have shown that the affinity matrix of the present invention can be used to separate therapeutic proteins (such as thrombin), antibodies, metals (such as cadmium), carbohydrates (such as cellulose), organic molecules (such as biotin) and cells (such as bacterial cells).

Oil body affinity matrices may also be used to separate cells of industrial or medical interest from a mixed population of cells. For example haematopoietic stem cells, which are a subpopulation of blood cells and are used in bone marrow transplantations and in stem cell gene therapies, may be separated from other blood cells using oil body based affinity technology. In recombinant DNA technology it is often required that cells in which recombinant DNA has been successfully introduced, known as transformed cells, are distinguished and separated from cells which failed to acquire recombinant DNA. Provided that part of the recombinant DNA expresses a cell surface protein which is complementary to a oil body based affinity ligand, it is possible to utilize oil bodies to separate transformed cells from untransformed cells. Oil body affinity technology may also be used to separate cellular organelles such as chloroplasts and mitochondria from other cellular material. Viral particles may also be separated from complex mixtures.

It is also possible to immobilize a class of proteins known as metalloproteins, which contain prosthetic groups that specifically bind ions. Examples of metalloproteins are haemoglobin, which binds iron, parvalbumnin which binds calcium and metallothionein a protein which binds zinc and other metal ions. It is envisioned that oil bodies could be used to scavenge metals from streams of flowing material, which might be water contaminated with the waste of metals from laboratories and industrial processes. Example 4 given below further illustrates this application. Other examples where proteins may be bioimmobilized and employed in a bioremediation strategy include the removal of phosphates, nitrates and phenols from waste streams. In part this approach may overcome the real or perceived limitations of bacterial bioremediation. In certain instances it may not be practical or necessary to rely on affinity partitioning technology to separate the oil body matrix from the target compound. In these instances, it is envisioned that oil bodies may be immobilized on a solid inert surface which could be a flat surface or the surface of a column. A solution containing the affinity ligand may then be passed over the surface coated with immobilized oil bodies whereupon selective affinity binding occurs. It is envisioned that immobilized oil bodies may be used in pipes and in ponds to assist in bioremediation.

The following examples illustrate various systems in which oil bodies can be used as affinity matrices. It is understood that the examples given below are intended to be illustrative rather than limiting.

EXAMPLES

Example 1

Purification of Thrombin

The following example demonstrates the utility of an oil body affinity matrix for the purification of thrombin. Thrombin is a serine protease which plays a central role in blood coagulation. It cleaves fibrinogen to produce fibrin monomers which polymerize to form the basis of a blood clot (Fenton 1981; *Ann. N.Y. Acad. Sci.* 370: 468–495). Alfa-thrombin consists of two polypeptide chains of 36 (A-chain) and 259 (B-chain) residues linked by a disulphide bridge. Degen et al. 1983; *Biochemistry* 22: 2087–2097). Hirudin, which is found in the salivary glands of the medicinal leech *Hirudo medicinalis*, is a very specific and potent inhibitor of thrombin. This inhibition is a result of the non-covalent binding of hirudin to specific parts of the alfa-thrombin chain. (Stone and Hofsteenge 1986; *Biochemistry* 25: 4622–4628).

The immobilized ligand is comprised of an isoform of hirudin fused to the 18 kDa Arabidopsis oleosin (oil body protein) (Van Rooijen et al., 1992; *Plant Mol. Biol.* 18: 1177–1179). Expression of the construct is regulated by the Arabidopsis 18 kDa oleosin promoter (Van Rooijen et al., 1994; *Plant Mol. Biol.* 18: 1177–1179). The sequence of the oleosin-hirudin fusion is shown in FIG. 2 and in SEQ ID NO:3.

Oleosin-Hirudin Construct

Oligonucleotide primers were designed based upon the reported sequence for a *Brassica napus* oleosin gene (Murphy et al. 1991, *Biochim. Biophys. Acta* 1088: 86–94) and used to amplify a fragment from *B. napus* genomic DNA through PCR. Using this fragment as a probe, a clone carrying a 15 kbp insert was identified and isolated from a EMBL3 Arabidopsis genomic library. Oligonucleotide primers were used to amplify a fragment from this insert containing the entire oleosin coding sequence and intron together with 840 basepairs of the 5' upstream region. The primers were designed so as to eliminate the translational stop codon and to introduce a PstI restriction endonuclease recognition site at the 5' end and a SalI followed by a PvuI site at the 3' end of the fragment. The fragment was end-filled and ligated into the SmaI site of the plasmid vector pUC19. A SalI-EcoRI fragment from plasmid pBI121 (Clontech) comprising the nopaline synthetase terminator sequence was then inserted to generate pOBILT.

A synthetic hirudin variant 2 (HV2) sequence was synthesized based upon reported sequence information (Harvey et al. 1986, *Proc. Natl. Acad. Sci. USA* 83: 1084–1088) but employing *B. napus* and Arabidopsis codon usage. The sequence was amplified using four overlapping oligonucleotide primers designed such that the resulting fragment possessed PvuI and SalI sites at the 5' and 3' ends respectively. This fragment was ligated into the SmaI site of the pUC19 plasmid vector to generate pHIR. The PvuI-SalI fragment from pHIR was then inserted into pUCOBILT between the oleosin and terminator sequences to form an in-frame fusion with the oleosin coding region giving pUCOBHIRT. The entire construct was subcloned into pBluescript KS+(pBIOBHIRT) and then into the PstI site of pCGN1559 plasmid (McBride and Summerfelt, 1990, *Plant Mol. Biol.* 14: 269–276) carrying a neomycin phosphotransferase gene under control of the 35-S CaMV promoter (pCGOBHIRT). This plasmid was introduced into *Agrobacterium tumefaciens*. The preparation of this plasmid is shown in FIG. 3.

Transformation and Regeneration

Procedures for the transformation of Agrobacterium and plants have been described previously. *Agrobacterium tumefaciens* was transformed with the above construct through electroporation (Dower et al., 1988; *Nucl. Acids Res.* 16: 6127–6145). The transformed bacteria were then used to transform cotyledonary explants of *Brassica napus*, followed by plant regeneration according to the methods of Moloney et al. (1989; *Plant Cell Reports* 8: 238–242). Transgenic plant were initially identified using a neomycin phosphotransferase assay and subsequently confirmed by expression of the oleosin-hirudin fusion as determined through northern and immunoblot analysis.

Preparation of Oil Bodies

Seed from either control (non-transgenic) plants or transgenic plants expressing the oleosin-hirudin fusion were homogenized in five volumes of cold grinding buffer (50 mM Tris-HCl, pH 7.5, 0.4 M sucrose and 0.5 M NaCl) using a polytron operating at high-speed. The homogenate was centrifuged at approximately 10×g for 30 min. to remove particulate matter and to separate oil bodies from the aqueous phase containing the bulk of soluble seed protein. Oil bodies were skimmed from the surface of the supernatant with a metal spatula and placed in one volume of fresh grinding buffer. To achieve efficient washing in subsequent steps, it was important to ensure that the oil bodies were thoroughly redispersed. This was accomplished by gently re-homogenising the oil bodies in grinding buffer with the polytron operating at low-speed. Using a syringe, the resuspended oil bodies were carefully layered underneath five volumes of cold 50 mM Tris-HCl, pH 7.5 and centrifuged as above. Following centrifugation, the oil bodies were again removed and the washing procedure repeated three times to remove residual contaminating soluble seed proteins. The final washed oil body preparation was resuspended in one volume of cold 50 mM Tris-HCl pH 7.5, redispersed with the polytron, and was then ready for use as an affinity matrix.

Affinity Purification of Thrombin

The purification of thrombin using the oleosin-hirudin fusion protein is shown schematically in FIG. 4. In order to evaluate the binding of thrombin, affinity matrices were prepared from transgenic *Brassica napus* seeds expressing the oleosin-hirudin fusion protein (4A4 seeds) (Parmenter et al. *Plant Molecular Biology* (1995) 29: 1167–1180) and from wild type *Brassica napus* cv Westar seeds. Binding of thrombin to both matrices was evaluated. Procedures for the preparation of washed oil bodies from seeds were the same as those described above. Solutions containing a range of thrombin activities between 0 and 1 units were mixed with 10 µl of a fixed amount of affinity matrix (prepared from a total of 10 mg of dried seeds; corresponding to approximately 100 µg of total oil body protein) in 500 µl binding buffer (50 mM Tris-HCl (pH 7.5); 0.1% (w/v) BSA). The oil body suspension was then incubated for 30 minutes on ice and centrifuged at 14,000 rpm for 15 minutes at 4° C. The buffer under the oil bodies (termed 'unternatant') containing the unbound, free thrombin was recovered using an hypodermic needle and assayed for thrombin activity as follows. A total of 250 µl of unternatant was added to 700 µl binding buffer and prewarmed to 37° C. Following the addition of 50 µl of 1 mM thrombin substrate N-p-tosyl-gly-pro-arg-p-nitroanilide (Sigma) to the unternatant, the change in optical density at 405 nanometers was monitored spectrophotometrically for 3 minutes. The concentration of thrombin in the assay mixture was determined employing a standard curve which was constructed using a set of thrombin samples containing known concentrations of thrombin. The values obtained from these assays were used to calculate the concentration bound thrombin assuming:

[bound thrombin]=[total thrombin]−[free thrombin]

The ratio of the concentration of bound over the concentration of free thrombin was plotted as a function of the concentration of bound thrombin (Scatchard plot). From these plots the dissociation constants of the affinity matrix were calculated following standard procedures (Scatchard, G. *Ann. N.Y. Acad. Sci.* (1949) 57: 660–672) and assuming: $K_a=1/K_d$. The dissociation constants of the affinity matrices were $3.22 \times 10^{-7}$ m for wild type and $2.60 \times 10^{-8}$ m for 4A4 oil bodies.

Figure 5:
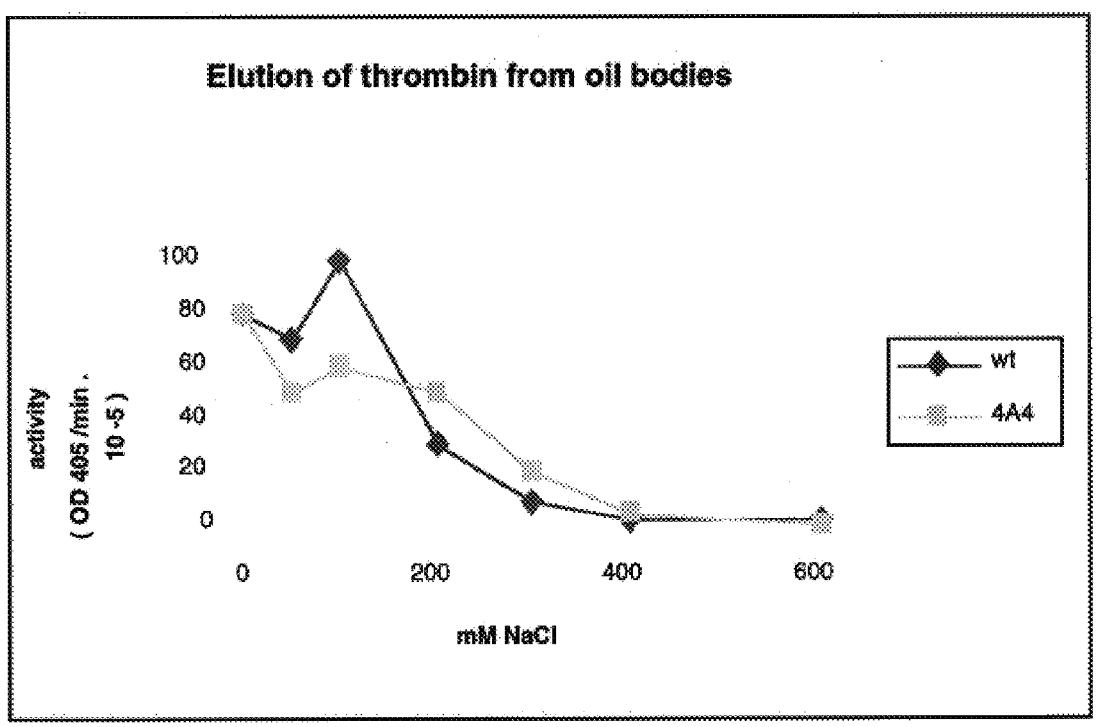
FIG. 5. NaCl elution profiles of thrombin from wild type and 4A4 oil body matrices transformed with a construct expressing an oleosin-hirudin fusion.

In order to evaluate the recovery of bound thrombin from the matrices a NaCl gradient was employed. The elution profile of thrombin bound to oleosin-hirudin oil body matrices was compared with the profile from thrombin bound to wildtype oil body matrices. Procedures for preparation of wild type oil bodies from wild type *Brassica napus* cv Westar seeds and for the preparation of oleosin-hirudin oil bodies from *Brassica napus* 4A4 seeds (Parmenter et al. *Plant Molecular Biology* (1995) 29: 1167–1180) were identical to those described above. Procedures for binding of thrombin to the matrices were as described above, except 100 µl aliquots of oil bodies were used to bind 0.5 units of thrombin. Oil body suspensions were left on ice for 30 minutes prior to centrifugation for 15 minutes at 4° C. and 14,000 rpm. The unternatant was assayed for (unbound) thrombin activity. The oil body matrix was then resuspended in binding buffer to which NaCl was added to a final concentration of 0.05 M. Starting with the 30 minutes incubation of the oil body suspension on ice, the procedure was repeated five times increasing the NaCl concentration in a stepwise fashion. The final NaCl concentrations used were 0.05 M, 0.1 M, 0.2 M, 0.3 M, 0.4 M and 0.6 M. The NaCl concentrations in the thrombin assay were kept constant at 150 mM. FIG. 5 shows the elution profiles obtained when wildtype oil bodies and 4A4 oil bodies were used.

Example 2

Use of Antibodies as Bivalent Ligands

Figure 6:
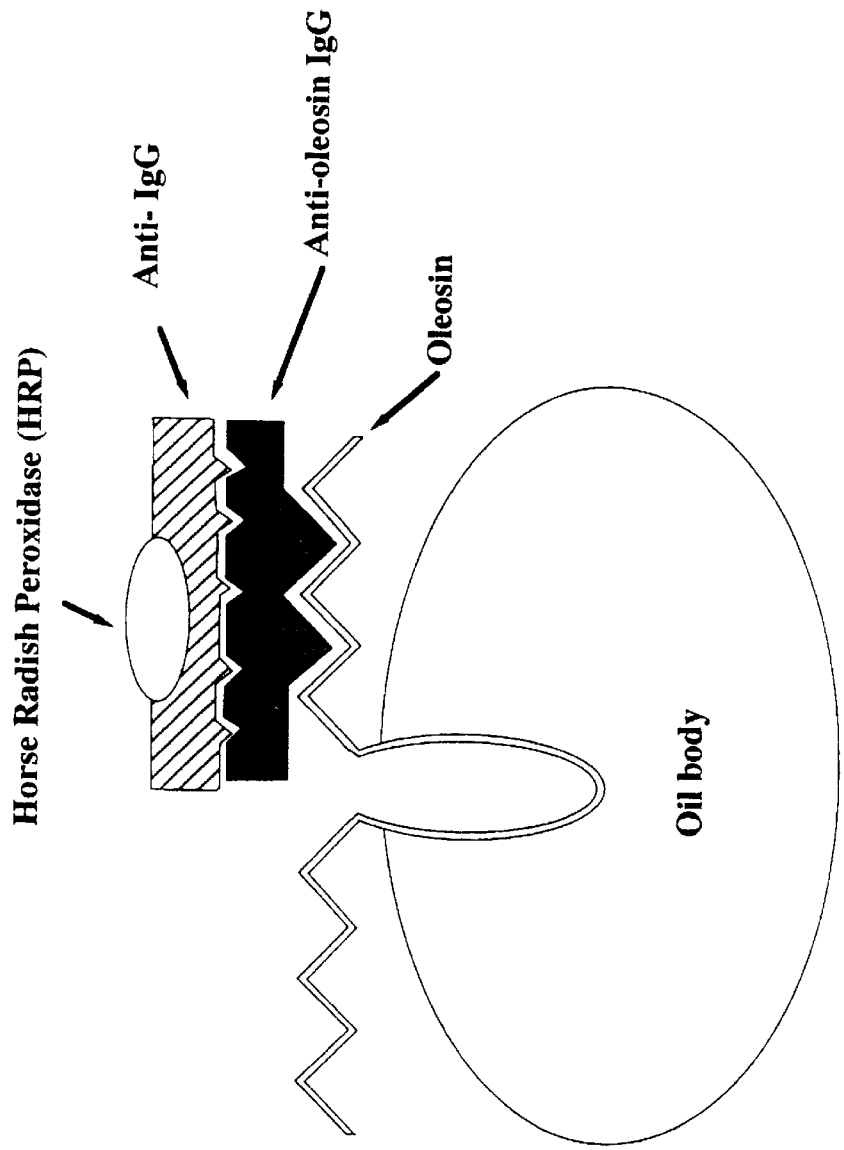
FIG. 6. Purification of a horseradish peroxidase conjugated anti-IgG antibody using an anti-oleosin antibody as a ligand. Schematic diagram illustrating the configuration of the oleosin/anti-oleosin/anti-IgG sandwich complex bound to an oil body.

Antibodies may be used as bivalent ligands by virtue of their affinity both for specific epitopes and for other antibodies or proteins (for example the *Staphylococcus aureus* protein A) which have affinity for immunoglobulins (IgGs). In this example, polyclonal anti-oleosin antibodies serve as a bivalent ligand and antibodies raised in rabbits against the anti-oleosin antibodies serve as the target. This example is illustrated schematically in FIG. 6.

Figure 7:
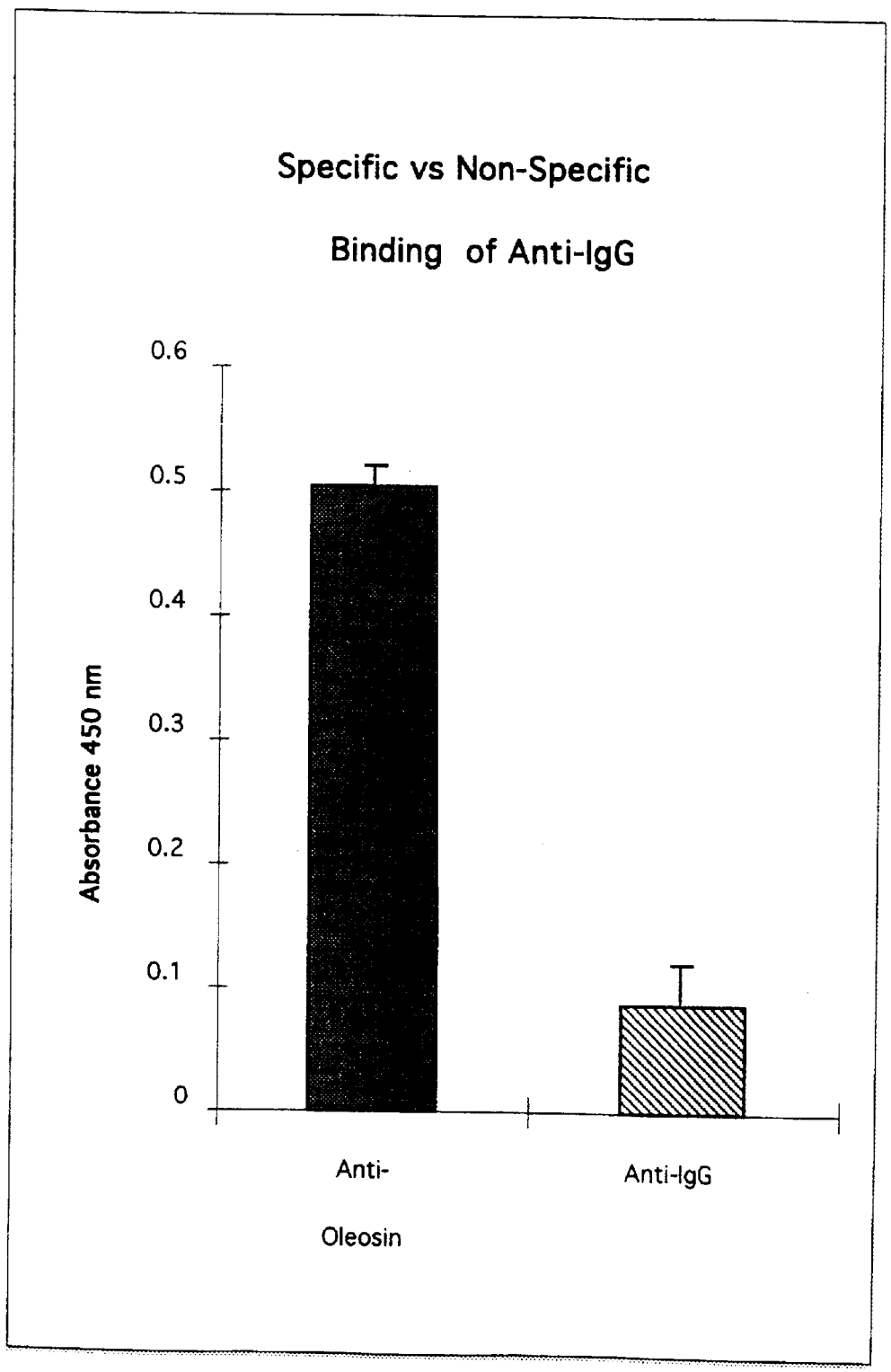
FIG. 7. Illustrates specific binding of anti-IgG antibodies to wild type oil bodies complexed with primary anti-oleosin antibodies as a ligand (left) and binding of anti-IgG antibodies to oil bodies which were not complexed with primary antibodies prior to binding with the secondary antibodies (right).

Oil bodies were prepared from 5 g of wild type *Brassica napus* cv Westar seeds following the procedure described in Example 1. Subsequently, oil bodies were washed twice with 100 mM glycine (pH 2.5), neutralized through two washes in binding buffer (50 mM Tris-HCl, pH 7.5) and resuspended in 5 ml of binding buffer. A 150 µl aliquot of the washed oil body preparation was combined with 500 µl of rabbit serum containing anti-oleosin antibodies (ligand antibodies), diluted 1:10 with binding buffer. The oil body suspension was mixed thoroughly and incubated for 1 h at 4° C. with agitation. Following incubation, unbound ligand antibodies were removed from the oil body suspension through three washes with 1 ml of binding buffer. Oil bodies were then combined with 500 µl of serum diluted 1:500 in binding buffer and containing anti-rabbit IgG antibodies (the target antibodies) conjugated with horseradish peroxidase (HRP) as a detection label (Sigma). This suspension was mixed and incubated under conditions identical to those used for the anti-oleosin antibody binding. As a control, target antibodies were incubated with oil bodies which had not been previously bound to ligand antibodies. Both samples were subsequently washed four times with 1 ml of binding buffer to remove unbound antibodies. Using binding buffer, the samples were equalized with respect to concentration of oil bodies as determined by measuring sample turbidity spectrophotometrically at 600 nm. To assay for bound target antibody, samples containing 5 µl of oil bodies were mixed with 1 ml of the HRP colorimetric substrate tetramethylbenzidine in 0.01% hydrogen peroxide and reacted for 10 minutes at room temperature. Reactions were stopped by the addition of 500 µl of 1 M $H_2SO_4$ and the absorbance at 450 nm was determined. Corrections for the presence of residual, unbound target antibody remaining after washing were made by assaying 5 µl of the final wash fraction. The results obtained for control and ligand bound oil body preparations are set forth in FIG. 7.

Example 3

Use of Oleosin-Specific Ligands

The use of an oleosin-specific ligand represents an alternative to the use of an antibody or genetically-engineered oleosin fusion proteins for the purification of recombinant target proteins. In this case, the target protein is fused to the oleosin-specific ligand and the endogenous oleosins present on the oil bodies of non-transgenic seeds serve as the complementary ligand-affinity matrix. In addition to eliminating the requirement for a transgenic line expressing an oleosin fusion, this approach increases the overall capacity of the affinity matrix, since all of the endogenous oleosins may now participate in binding.

Oleosin-specific ligands may be identified and isolated from a peptide phage display library screened with oleosin protein. Since the extreme hydrophobicity of the oleosin central domain can result in aggregation and precipitation of the protein when removed from oil bodies, a mutant protein lacking this domain may be used for screening. This has little effect on the efficacy of the ligand, as only the hydrophillic portions of the oleosin are exposed to the cytoplasm (i.e. the N- and C-termini). Hence, these are the only regions available for binding to a ligand. Once isolated, the ligand may be fused to a common reporter protein, green fluorescent protein (GFP) (Prasher, 1995, *Trends Genet.* 11:320–323), to demonstrate purification.

Removal of the Oleosin Central Domain

Oligonucleotide primers specific for the Arabidopsis oleosin gene described above can be used to amplify an oleosin gene from a *B. napus* cDNA library (van Rooijen 1993, *Ph.D. Thesis*, University of Calgary). Primers flanking sequences encoding the N-terminal 62 amino acids and the C-terminal 55 amino acids, may be used to amplify sequences for the respective N- and C-terminal oleosin domains in separate reactions. Additionally, the primer for the 5' end of the N-terminal domain contains a sequence for a thrombin recognition site to enable cleavage of the fusion protein as described below. The resulting fragment was ligated into the SmaI site of the bacterial expression vector pEZZ 18 (Pharmacia). This vector contains sequences encoding a signal peptide for protein secretion into the periplasm, and synthetic IgG binding domains derived from protein A to facilitate protein purification, downstream of the multiple cloning site.

Expression and Purification of the Oleosin Deletion Construct

The vector carrying the deletion mutant construct is introduced into *E. coli* using standard methods and transformants selected. A culture of the transformed bacteria can be induced to express the synthetic protein A-mutant oleosin fusion protein by addition of 1 mM IPTG. Induced cells may be pelleted and resuspended in 5 mM $MgSO_4$ causing lysis of the periplasmic membrane through osmotic shock. The lysed cells are centrifuged and the supernatant containing the secreted protein is loaded on to a column containing IgG-coupled sepharose. After washing to remove unbound protein, the column is loaded with a buffer containing 50 mM Tris-HCl, pH 7.5, 150 mM NaCl and 1.0 U/ml of purified Bovine thrombin (Sigma) to cleave the mutant oleosin from the synthetic protein A. Following incubation at 37° C. for 4 h, the column is drained and the eluate passed through a column of heparin-coupled sepharose to remove thrombin. The eluate from this column, containing the mutant oleosin protein, is recovered and purity of the protein examined through gel electrophoresis followed by staining with Coomassie blue R250.

Generation of a Peptide Combinatorial Library

A random peptide combinatorial library may be generated according to the methods of Scott and Smith (1990; *Science* 249: 386–390). Briefly, the PCR is used to amplify a synthetic DNA fragment containing the degenerate sequence $(NNK)_6$; where 'N' represents an equal mixture of deoxynucleotides G, A, T, and C, and K represents an equal mixture of deoxynucleotides G and T. The degenerate sequence encodes for hexameric peptides among which are represented every possible combination of the 20 amino acids and amber stop codon. The PCR product is ligated into the gene III sequence of the filamentous bacteriophage fUSE and the resulting phagemid introduced into *E. coli* through electroporation.

Identification and Isolation of Oleosin-Specific Ligands

The peptide phage display libraries are amplified, concentrated and stored in aliquots of $10^{12}$ tdu/ml. Purified mutant oleosin protein is biotinylated using a thiol-cleavable linker (S-S biotin, Pierce) and purified by size exclusion chromatography. Aliquots of the peptide phage display library containing $5 \times 10^{11}$ tdu in two ml are screened with the biotinylated protein at a concentration of 50 nM. Phage binding the mutant oleosin protein are recovered using streptavidin-coated paramagnetic beads. Following washing, the phage are eluted through the addition of 50 mM dithiothreitol which cleaves the disulphide bond. The eluted phage are then incubated with an excess of log-phase F+ *E. coli*. Aliquots of the infected cells are plated to determine the phage titre and the remaining cells used in successive rounds of amplification and screening. Following enrichment of the eluted phage by 3–4 orders of magnitude, individual phage are selected and tested for binding to mutant oleosin by direct ELISA. Binding by phage is detected using anti-phage antibodies (Crosby and Schorr, 1995, In *Annual Review of Cell Biology*). Single stranded DNA is isolated from phage exhibiting binding and the peptide-encoding sequence determined.

Affinity Purification with Oleosin-Specific Ligands

The sequence for an oleosin ligand isolated as described above is fused in-frame upstream the sequence for gfp10 (Prasher et al., 1992, *Gene* 111: 229–233) encoding GFP and the construct ligated into the bacterial expression vector pKK233 (Pharmacia). Soluble protein is extracted through sonication of cells induced to express the ligand-GFP fusion, and adjusted to a concentration of 10 mg/ml in 50 mM Tris-HCl, pH 7.5.

Twenty ml of the protein solution is mixed with 2 ml of oil bodies prepared as described above, from seeds of non-transgenic plants. The mixture is incubated at 4° C. for 30 min with agitation to allow binding and then centrifuged to separate the oil bodies and soluble fraction. The amount of GFP remaining in the soluble fraction after removal of oil bodies is determined by fluorescence spectrofluorometry at a wavelength of 508 nm and compared with that in the original bacterial extract. The amount of bound GFP is calculated to determine the capacity of the matrix.

The oil bodies are washed twice in 20 ml of 50 mM Tris-HCl, pH 7.5, resuspended in 2 ml of the same buffer and divided into 20 aliquots of 100 µl. Conditions for the elution of ligand-GFP fusion protein are determined by adding 1 ml of solutions ranging in pH from 2–10 and in NaCl concentration from 0–1 M to different aliquots. After mixing and incubation at 4° C. for 30 min, the oil bodies are removed and the soluble fractions collected. The amount of ligand-GFP fusion protein in the soluble fraction is determined by fluorescence spectrophotometry.

Example 4
Removal of Heavy Metal Ions

The following example demonstrates the utility of oil body affinity matrices for the recovery/removal of non-protein targets from complex solutions. For the purpose of this example the metallothionein/$Cd^{++}$ ligand pair was used. However other metal binding proteins such as phytochelatins (Rauser, 1990; Ann. Rev. Biochem; 59: 61–86) and metal ions including $Cu^{++}$ and $Zn^{++}$ could also be used.

Oleosin-Metallothionein Fusion

Figure 9:
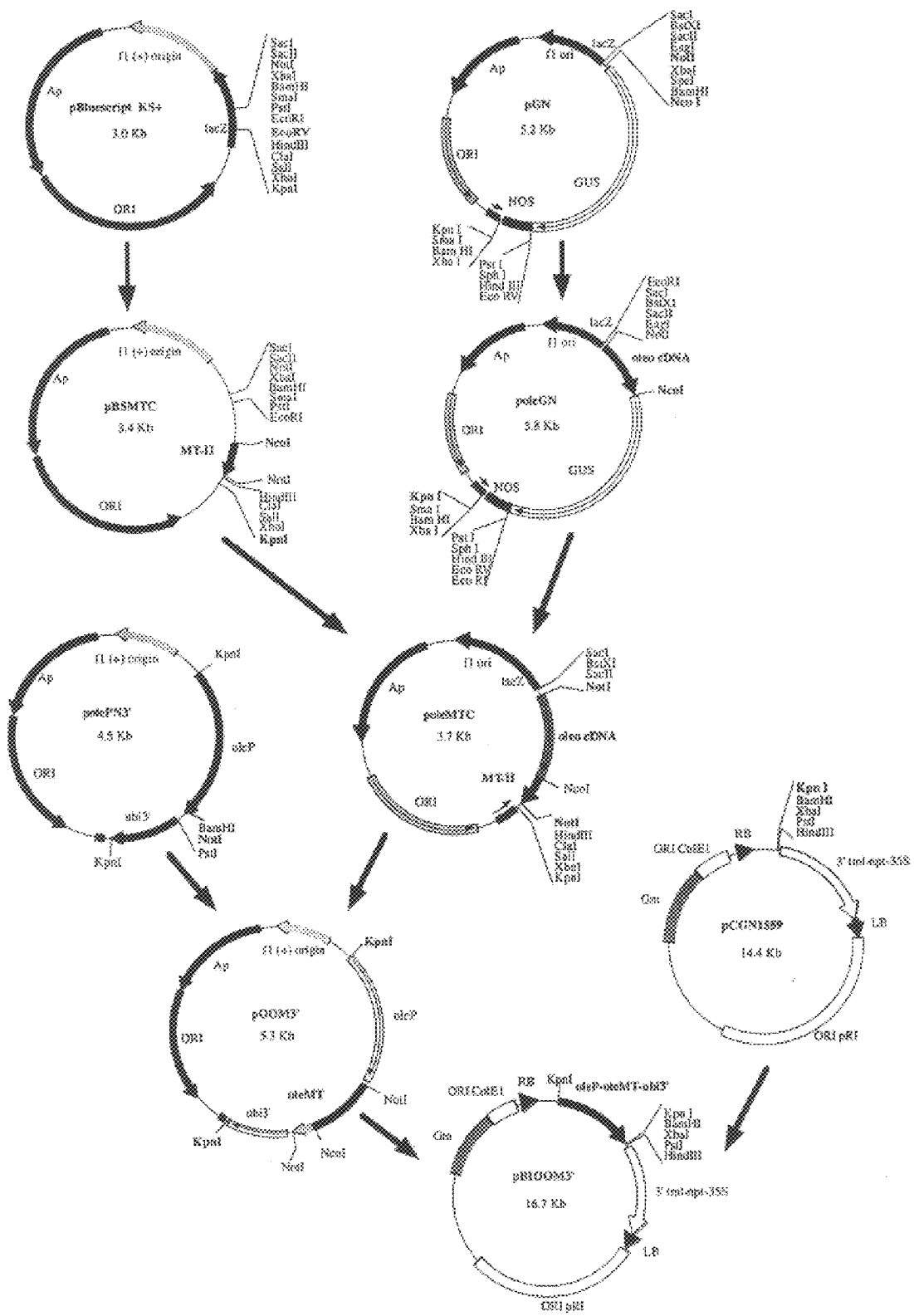
FIG. 9. Outline of the steps employed in the construction of pBIOOM3' containing the entire oleosin-metallothionein construct.

An oleosin gene from a B. napus cDNA library (van Rooijen 1993, Ph.D. Thesis, University of Calgary) was amplified through PCR with oligonucleotide primers designed so as to create NotI and NcoI sites at the 5' and 3' ends of the gene respectively. The resulting fragment was digested and placed into the NotI/NcoI sites of pGN to yield plasmid poleGN. The human metallothionein gene, mt-II (Varshney and Gedamu, 1984, Gene, 31: 135–145) was amplified using oligonucleotide primers designed to create a unique NotI site at the 3'-end of the gene. The resulting PCR product was subcloned into the blunt-end EcoRV site of pBluescript KS+ to form pBSMTC. The mt-II gene was then excised from this plasmid and subcloned into the NcoI/KpnI sites of poleGN replacing the GUS-NOS region to generate pOLEMTC. The 773 base oleosin-MT fusion of pOLEMTC was excised with NotI digestion and inserted into the unique NotI site of polePN3' between the oleosin promoter (oleP; Van Rooijen et al., 1992, Plant Mol. Biol 18: 1177–1179) and the P. crispum ubi4-2 gene terminator (ubi3'; Kawalleck et al., 1993, Plant Mol. Biol, 21: 673–684.) to generate pOOM3'. After the fusion was determined to be in the correct orientation, pOOM3' was digested with KpnI to release the oleP-oleMT-ubi3' insert. This expression cassette was inserted at the KpnI site of the binary vector pCGN1559 to yield the final construct pBIOOM3'. The sequence of the oleosin-metallothionein fusion is shown in FIG. 8 and SEQ ID NO:6. The construction of plasmid pBIOOM3' is shown in FIG. 9.

Transformation and Regeneration

Transgenic B. carinata plants expressing the oleosin-metallothionein fusion were created using transformation and regeneration protocols as described in Example 1.

Oil Body Preparation

Washed oil bodies were prepared from B. carinata seeds of transgenic and control plants as described in Example 1.

Removal of Cd++ from Solution Using an Oil Body Affinity Matrix

Figure 10:
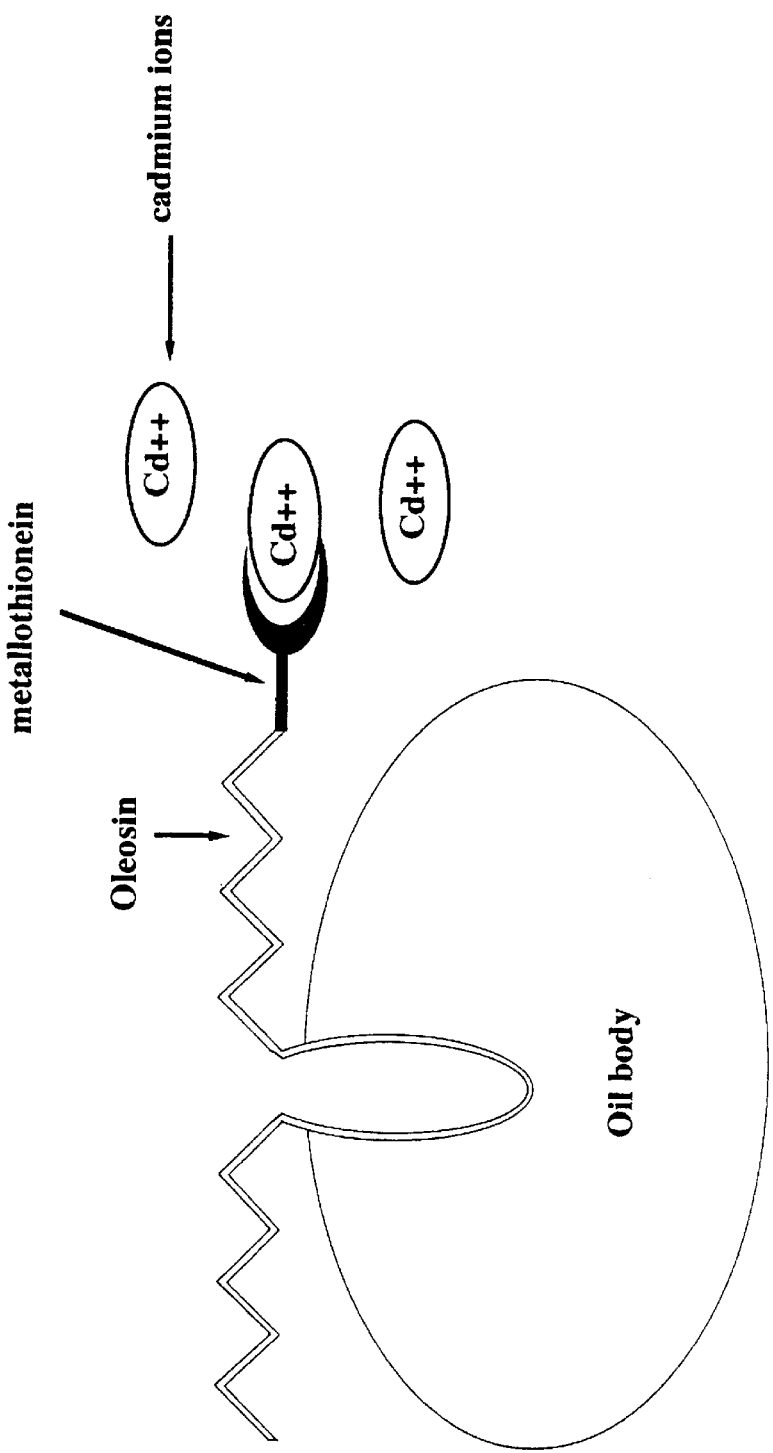
FIG. 10. Schematic diagram illustrating the configuration of the oleosin-metallothionein fusion protein on the oil body and binding of cadmium ions.

The use of the oleosin-metallothionein fusion to bind cadmium ions in solution is shown schematically in FIG. 10.

A solution of 10 µM $CdCl_2$ in 10 mM Tris-HCl, pH 7.2 containing 0.01 µCi/ml $^{109}Cd$ was prepared. A 1 ml aliquot of this $CdCl_2$ solution was thoroughly mixed with 100 µl of washed oil bodies (1.6 mg oil body protein) prepared from seeds expressing the oleosin-metallothionein fusion protein and incubated at 22° C. for 1 hr. Following centrifugation for 5' at 10,000×g to separate the oil bodies from the aqueous phase and 2 washes in 1 ml of 10 mM Tris-Cl, pH 7.2, the amount of $^{109}Cd^{++}$ remaining bound to oil body fraction was determined using a gamma-counter (Cobra auto-gamma, Canberra Packard, Canada). An identical experiment was performed with oil bodies from non-transgenic seeds to detect and correct for non-specific binding of Cd ions to the matrix.

$Cd^{++}$ ions were eluted from the oil body metallothionein affinity matrix by mixing of the oil body fraction with 1 ml of 100 mM glycine (pH=3.0) buffer (Pazirandeh et al., 1995; Appl. Microbiol. Biotechn. 43: 1112–1117). Following centrifugation for 5 min. At 10,000 xg, the oil body fraction was removed and assayed for bound $Cd^{++}$ ions as above. FIG. 11 shows Cd binding and elution from the affinity matrix.

Example 5
Separation of Whole Cells

The following example illustrates the capacity of oil bodies to immobilize whole cells. One potential for the use of bacterial cell separation lies in the utility for diagnostics. It is also desirable to separate unique eukaryotic cells such as lymphocytes and stem cells from complex mixtures of cells where the cell type of interest is present in relatively low numbers.

Binding of Staphylococcus aureus to Oil Bodies via protein A

For the purpose of this example, S. aureus cells, which express protein A as a surface antigen were mixed with oil bodies with varying amounts of polyclonal anti-oleosin antibodies.

Preparation of Oil Bodies

Seeds of B. napus cv Westar were surface sterilized in bleach, rinsed and ground with a mortar and pestle in grinding buffer (50 mM Tris pH 7.5, 0.4 M sucrose and 100 mM glycine). The homogenate was filtered through Miracloth into sterile 15 ml Corex tubes. The filtered homogenate was then centrifuged for at 4° C. for 10 min at 10,000×g. The oil body fraction was removed and resuspended in 50 mM Tris pH 7.5 and 0.4 M sucrose and washed two times using the same buffer. Aliquots of 1 ml oil bodies were transferred to 1.5 ml Eppendorf tubes and centrifuged at room temperature for 10 min at 16,000×g. The oil bodies were washed in 50 mM Tris pH 7.5 and 0.4 M sucrose 5–6 more times until no visible pellet was observed.

Binding of S. aureus Cells to Anti-oleosin Coated Oil Bodies

Figure 12:
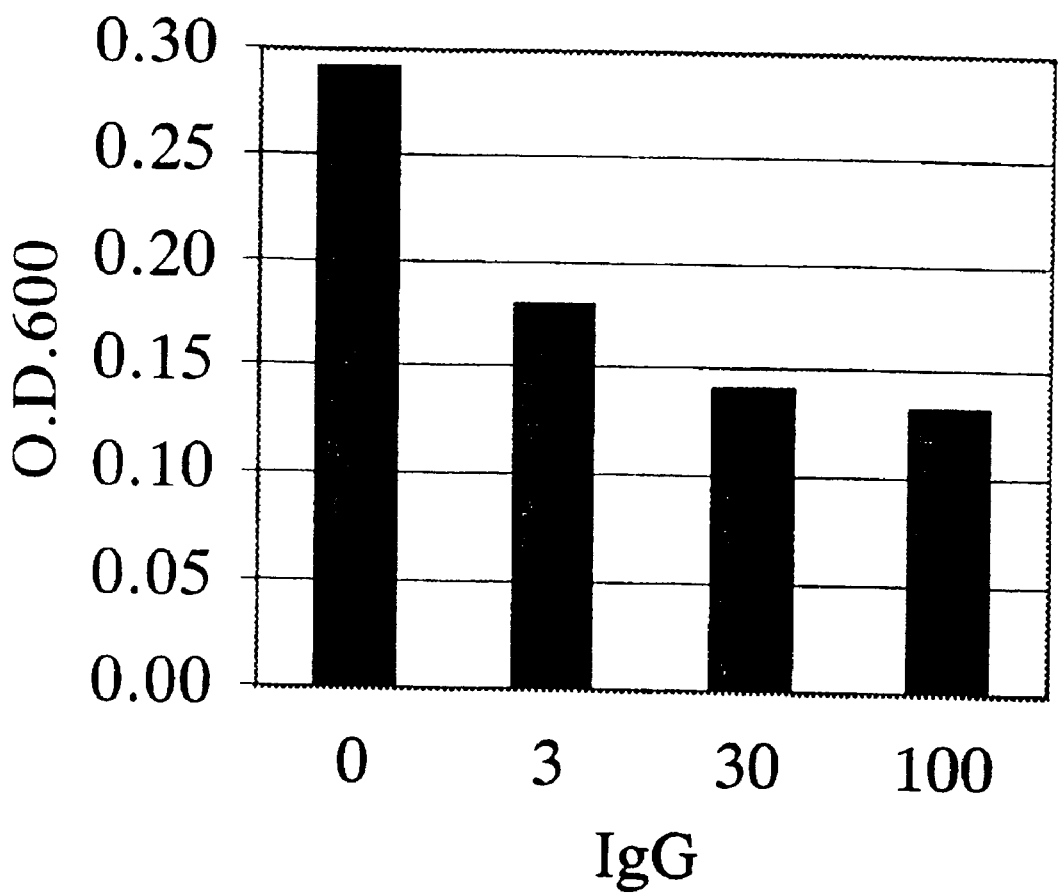
FIG. 12. Illustrates the binding of protein A expressing *S. aureus* cells to oil bodies treated with varying amounts of anti-oleosin IgGs. Bars represent $OD_{600}$ readings obtained following the procedures as described in Example 5 and using varying amounts of IgGs (0 µl, 3, µl, 30 µl, 100 µl of added IgG).

Formalin fixed S. aureus cells (Sigma, P-7155) were washed 3–4 times in 50 mM Tris-Cl pH 7.5. and resuspended. Washed oil bodies (300 gl) and S. aureus cells (were mixed with varying amounts of anti-oleosin IgGs (50 µl). After mixing and incubating at room temperature for 2 hrs, the mixtures were centrifuged at room temp at 16,000×g for 5 min. The oil body fraction and unternatant were carefully removed and the cell pellet was washed twice in 1 ml 50 mM Tris-Cl pH 7.5. The walls of the tube were wiped with a tissue to remove traces of oil. Subsequently the drained cell pellets were resuspended in 1 ml of water and the $OD_{600}$ were determined. FIG. 12 is a representative experiment showing the decrease in the amount of cells present in the cell pellet as the concentration of anti-IgGs present in the oil-body S. aureus mixture increases.

Differential Binding of Two Strains of Staphylococcus aureus

In this experiment an oil body affinity matrix is employed to demonstrate differential binding of two strains of Staphylococcus aureus. Formalin fixed S. aureus strains, one expressing the IgG binding surface antigen protein A and one lacking protein A, are commercially available from Sigma. Dilute aliquots of both S. aureus strains of equal $OD_{550}$ could be prepared. To each of these aliquots control oil bodies from untransformed plants or oil bodies mixed with anti-oleosin antibodies could be added. Following incubation for an appropriate length of time at an appropriate temperature, the samples could be centrifuged to pellet unbound bacterial cells and to separate the oil body fraction. The oil bodies could be decanted, vortexed and the $OD_{550}$ could be determined. The pellets could be resuspended and the $OD_{550}$ of the unternatant could be determined. It is anticipated that only in the sample containing the S. aureus strain expressing protein A and the oil body complexed with anti-oleosin antibodies, fractionation of these cells to the oil body fraction will be observed. Binding of the cells to the oil body could be further demonstrated by lowering of the pH of the oil body fraction. Subsequent to centrifugation the release of cells from the oil bodies could be evidenced by the presence of a pellet and/or an increase in $OD_{550}$ upon resuspension of the pellet.

Separation of *Staphylococcus aureus* from *E. coli*

A viable *S. aureus* strain could be mixed with varying quantities of cells of an *E. coli* strain having a specific antibiotic resistance. The mixed bacterial sample could be vortexed with control antibodies and with oil bodies which have been complexed with anti-oleosin antibodies. After incubation for an appropriate length of time and at an appropriate temperature oil bodies could be washed and the unternatant and oil bodies could be directly titrated and selectively plated on blood agar for *S. aureus* growth and on LB plates for *E. coli* growth. The enrichment or actual separation obtained could be determine by an estimate of colony forming units.

Identification of Pathogens Present in Low Concentrations in a Complex Mixture

For diagnostic purposes it is often desirable to concentrate bacterial or viral pathogens which invade human or animal tissues in low numbers. An oil body affinity matrix could be used to enrich for these pathogens, so that they could subsequently be identified and characterized.

Pathogens often specifically bind to human or animal cells through the interaction with a receptor or surface protein. Oleosin could be fused to the human or animal protein ligand and recombinant oil bodies could be employed to immobilize the pathogens. Examples of the formation of protein complexes formed between proteins of human and pathogenic origins known to the prior art include: human fibrinogen or fibrin specific domains which bind to *S. aureus* protein clumping factor A (clf-A) (McDevitt et al. 1995; *Mol. Microbiol.* 16; 895–907); human decay accelerating factor (DAF) to which urinary and intestinal tract pathogenic *E. Coli* bind (Nowicki et al. 1993*: J. Of Experim. Med.* 178: 2115–2121); a human cell ligand which is expressed in the carcinoma cell line Caco-2 and which binds uniquely to the 28 kD *Klebsiella pneumoniae* fimbria protein KPF-28 (Di Maretino et al., 1996; Infect. and Immun. 64: 2263–2266) and human cell extracellular matrix fibronectin specific domains which complex specifically with *Streptococcus pyrogenes* adhesin (protein F) (Ozeri et al., 1996; EMBO J. 15: 989–998).

Example 6
Separation of Small Organic Molecules

This example describes how an oil body affinity matrix may be used for the recovery/removal of small organic molecules from solution. By way of example, the small organic molecule, biotin, is purified using avidin as a ligand.

Construction of Avidin Ligands

Avidin is a protein synthesized by avian species and exhibits an extremely high affinity for biotin, a natural co-factor for many carboxylases. Preparations of purified avidin (commercially available from Sigma) can be conjugated chemically to anti-oleosin antibodies using standard procedures known to those skilled in the art. This approach would yield a bivalent avidin ligand suitable to demonstrate affinity based removal of biotin. Alternatively, an oleosin-avidin gene fusion may be utilized. The gene encoding avidin in chicken (*Gallus gallus*) has been identified and its sequence has been determined (Beattie et al., 1987, *Nucl Acids Res.* 15: 3595–3606). Based on the sequence the gene for avidin could be synthesized chemically or through the PCR and fused to the *B. napus* oleosin (van Rooijen, 1993, *Ph.D. Thesis*, University of Calgary) as described in example 4. Streptavidin, an analogous bacterial biotin binding protein, could also be employed.

Oil Body Preparation

Washed oil bodies would be prepared from seeds of transgenic plants and/or control plants as described in example 1.

Binding of Bivalent Avidin-Oleosin Ligand

Binding of anti-oleosin antibodies and removal of unbound ligand will be as detailed in example 3.

Removal of Biotin from Solution

Solutions containing known concentrations of biotin could be combined with a fixed amount of oil bodies complexed with an anti-oleosin antibodies conjugated with avidin. Following binding, the mixture would be centrifuged to separate oil body and aqueous fraction. The amount of biotin remaining in the aqueous fraction is determined by competitive ELISA using anti-biotin antibodies conjugated to horse radish peroxidase (HRP). The amount of bound biotin may be calculated assuming:

[bound biotin]=[total biotin]-[free biotin]

From the obtained values, the dissociation constants can be determined as described in example 2. As a control, an identical experiment could be performed with oil bodies bound to anti-oleosin antibodies which have not been conjugated with avidin. If desired, biotin could be released from the oil body-avidin matrix through competitive elution using an excess of 2-(4'-hydroxybenzene) benzoic acid (HABA). Elution may also be aided by employing a genetically engineered mutant of avidin which exhibits a lower affinity for biotin. Such mutants have been described for the analogous biotin binding protein from bacteria, streptavidin (Chilkoti et al., 1995; Bio/Technol. 13: 1198–1204).

Example 7
Separation of Carbohydrates

The following example describes the utility of oil body matrices for the recovery of carbohydrates from complex biological mixtures. In this example the inventors demonstrate that an oil body immobilized cellulase is capable of binding cellulose.

Oleosin-Cellulose Binding Domain Fusion

Several of the cellulases produced by the bacterium *Cellulomonas fimi* contain discrete cellulose binding domains (CBDs). These CBDs independently bind to cellulose even when they are separated by proteolytic cleavage or genetic manipulation from the catalytic domain of the enzyme. Plasmid pUC18-CBDPT contains a fragment coding for the CBD of the beta-1,4-glucanase (Gilkes et al., 1992, *Journal of Biol. Chem.* 267: 6743–6749) and could be used to construct an oleosin-CBD gene fusion. A DNA fragment encoding the CBD domain could be isolated from pUC18-CBDPT using appropriate restriction enzymes or using the PCR. Alternatively, the CBDs of other cellulases from *C. Fimi* or cellulases from other sources could be used. An oleosin gene from *B. Napus* isolated from a cDNA library (van Rooijen, 1993, *Ph.D. Thesis*, University of Calgary) was cloned in pGN using the PCR and yielding plasmid pOLEGN as described in example 4. An in-frame gene fusion between the oleosin gene and the CBD gene could be generated using standard molecular techniques known to those skilled in the art. The final construct would comprise the CBD domain translationally fused immediately downstream of the oleosin.

Transformation and Regeneration

In order to introduce the fusion gene construct in plants, it would be subcloned in a binary vector, such as pCGN1559. Transgenic plants which express the oleosin-CBD fusion could be generated as described in example 1.

Oil Body Preparation

Washed oil bodies could be prepared from the seeds of transgenic and control wild type plants as described in example 1.

Removal of Cellulose from Solution Using an Oil Body Affinity Matrix

In order to evaluate binding of cellulose to the oil body affinity matrix, the binding capacities of oil bodies of wild type and transgenic plants are compared. Oil bodies could be mixed with appropriately buffered solutions containing a range of cellulose concentrations. The oil body suspension could then be incubated for an appropriate length of time and at an appropriate temperature. Upon centrifugation, the unternatant could be recovered and assayed for cellulose concentrations. The concentrations bound cellulose and free cellulose could be calculated assuming:

[bound cellulose]=[total cellulose]−[free cellulose]

The ratio of the concentration bound over the concentration free cellulose could be plotted as a function of the concentration of bound cellulose. From these plots dissociation constants could be calculated following standard procedures (Scatchard, G. *Ann. N. Y. Acad. Sci.* (1949) 57: 660–672) and as detailed in example 2.

Example 8

Separation of Nucleic Acids

The following example describes a method in which oil bodies are employed to bind single stranded (SS) nucleic acids.

Isolation of Single Stranded Nucleic Acids

A method for capturing SS nucleic acids may be used in diagnostics, such as plant viral disease, or in research applications where non-reannealed SS nucleic acids need to be selectively removed from solutions such as in hybridization reactions for differential screening of expressed genes. Oleosins could be fused with SS DNA or RNA binding proteins or specific domains thereof and could be used to trap SS nucleic acids for identification or further amplification. Well characterized SS nucleic acid binding proteins include: Agrobacterial Ti plasmid Vir E2 protein (Zupan et al., 1995, *Plant Physiol.* 107: 1041–1047); Tobacco Mosaic Virus (TMV) movement protein P30 (Citovsky et al., 1990; *Cell* 60: 637–647; Waigmann et at., 1994 *Proc Natl. Acad. Sci* (*USA*) 91: 14333–1437); Cauliflower Mosaic Virus coat protein (Thompson et al., 1993; *J. Gen. Virol* 74: 1141–1148) and *E. Coli* RecA and single stranded binding (SSB) proteins (Radding, 1991 *J. Biol. Chem.* 266; 5355–5358), Example 9

Separation of Recombinant Proteins

Figure 15:
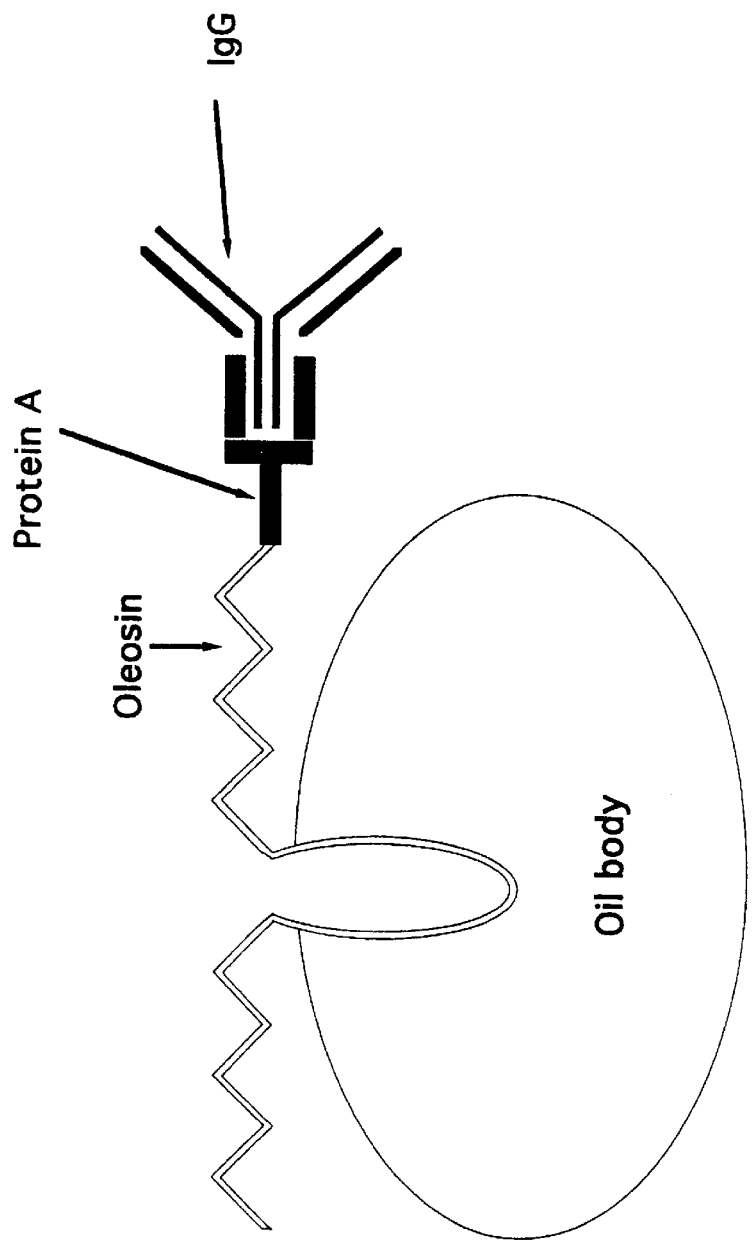
FIG. 15. Schematic diagram illustrating the configuration of the oleosin-protein A fusion protein on the oil body and binding of the immunoglobulin.

The following example further demonstrates the utility of an oil body affinity matrix for the purification of recombinant target proteins. For the purpose of this example, the IgG/protein A ligand pair has been chosen. The construct employed consists of a protein A domain which was fused to the 18 kDa Arabidopsis oleosin (Van Rooijen et al., 1992; *Plant Mol. Biol.* 18: 1177–1179). Oil bodies containing oleosin-protein A fusion proteins were isolated and used to demonstrate specific binding of rabbit-anti-mouse IgGs conjugated to Horse Raddish Peroxidase (HRP). The configuration of the oleosin-protein A fusion on the oil body and binding of IgG to the fusion is shown in FIG. 15.

The Oleosin-Protein A Fusion

A synthetic protein A sequence encoding a protein capable of binding to IgG was synthesized based on reported sequence information (pRIT2T, protein A gene fusion vector; Pharmacia) and was amplified through the PCR. Each primer used in the PCR contained restriction sites 5' to the protein A-specific sequence in order to facilitate cloning. The reverse primer (i.e. the primer in the antisense direction) also contained a translational stop codon following the coding sequence. FIG. 13 shows the position of the PCR primers relative to the protein A sequence. (The protein A sequence and the primer sequences are also separately shown in SEQ ID NO:8, SEQ ID NO:10 and SEQ ID NO:11 respectively). The resulting fragment was ligated into a pUC19 plasmid carrying the Arabidopsis oleosin gene comprised of an 867 bp upstream promoter region followed by the coding region (with its associated intron) from which the translational stop codon had been removed. The 3' end of the construct contains the nopaline synthase transcriptional terminator. A spacer sequence encoding a recognition sequence for the endoprotease thrombin was incorporated immediately downstream of the oleosin coding sequence. The protein A gene sequence was introduced between this spacer sequence and the terminator sequence. In the final expression construct the oleosin and protein A coding regions were fused in the same reading frame. The entire construct (FIG. 14 and SEQ ID NO:12) was then excised from the pUC19 plasmid and subcloned into the plant transformation vector pCGN1559 (McBride and Summerfelt, 1990, *Plant Mol. Biol.* 14: 269–276) carrying a neomycin phosphotransferase gene under the control of the 355 CaMV promoter The resulting plasmid was introduced in Agrobacterium (strain EHA101).

Transformation and Regeneration

Plants were transformed and regenerated as described in example 1. Transgenic plants were initially identified using a neomycin phosphotransferase assay and subsequently confirmed by expression of protein A fusions through immunoblot analysis.

Preparation of Oil Bodies

Oil bodies from the transgenic *B. napus* and *B. carinata* lines expressing the oleosin-protein A fusion were prepared following the procedure described in example 1.

Binding of Oleosin-Protein A Fusions to IgG

Figure 16:
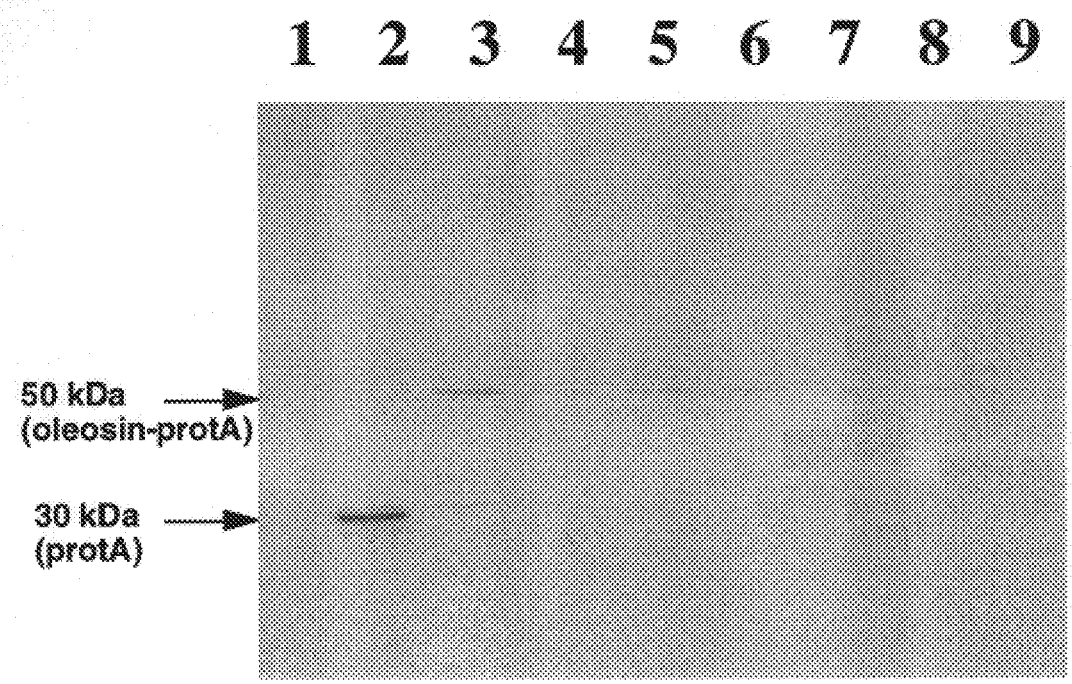
FIG. 16. A western blot illustrating the binding of HRP-conjugated mouse anti-rabbit antibodies to oil body protein extracts obtained from transgenic *B. napus* lines expressing oleosin-protein A fusion proteins. Shown on a Western blot probed with an HRP-conjugated antibody are oil body protein extracts from transgenic lines, opa 30 (lane 3), opa 31 (lane 4), opa 34 (lane 5), opa 36 (lane 6), opa 47 (lane 7), opa 93 (lane 8), all expressing an oleosin-protein A fusion protein and a control untransformed *B. napus* line (lane 9), as well as lysates of *E. coli* DH5α transformed with pRIT2T expressing protein A (lane 2) and untransformed *E. coli* DH5α (lane 1).

Oil body protein extracts (20 μg/aliquot) from various transgenic *B. napus* lines expressing oleosin-protein A fusion proteins were subjected to polyacrylamide gelelectrophoresis and subsequently transferred to a PVDF membrane following standard procedures. The membrane was then probed with a HRP-conjugated mouse anti-rabbit antibody and visualised following the procedure as outlined in Antibodies, a laboratory manual (Harlow and Lane, 1988, Cold Spring Harbor). In FIG. 16 the stained PVDF membrane is shown A 50 kDa protein (predicted molecular mass of the oleosin-protein A fusion protein: 48,801 Da) was specifically detected in the protein extracts of all of the six transgenic *B. napus* lines tested. Untransformed control plants did not exhibit HRP activity, while the a 30 kDa protein (predicted molecular mass 29,652 Da) was present in a bacterial lysate transformed with pRIT2T encoding protein A and undetectable in the untransformed lysate.

Binding and Elution of IgGs to Oil Bodies Containing Oleosin-Protein A Fusion Proteins Washed oil bodies (10 mg/ml protein) were prepared from wildtype *B. napus* and a transgenic *B. napus* line transformed with a construct expressing an oleosin-protein A fusion protein as described in example 1 and suspended in 10 mM Tris-Cl pH 8.0. A volume of 2 μl (±34 μg) of HRP-conjugated rabbit anti-mouse antibodies (Sigma, cat no A9044) was added to 500 μl of the washed oil body preparation and the suspension was incubated for 1 hr at room temperature or overnight at 4° C. The samples were then centrifuged for 15 min at 16,000×g and the undernatant was removed. Subsequently, the oil bodies were thoroughly resuspended in 500 μl 10 mM Tris-Cl pH 8.0 using a pestle. This washing step in Tris-Cl was repeated 4 times (henceforth termed washed oil body preparation). A 5 μl aliquot from the washed oil body preparation was washed a fifth time and then assayed for HRP activity.

HRP assays were carried out by adding 1 μl of the washed oil body preparation to 1 ml of HRP assay mix (9.8 ml of 0.1 M NaOAc, 0.2 ml of 2.5 mg/ml Trimethylbenzidine in DMSO, 4 μl $H_2O_2$) and incubating the mixture for 5 min at room temperature. The reaction was then stopped by adding 0.5 ml 1M $H_2SO_4$. The samples were filtered through a 0.22 μm filter and subsequently the $OD_{450}$'s were determined spectrophotometrically.

Figure 17:
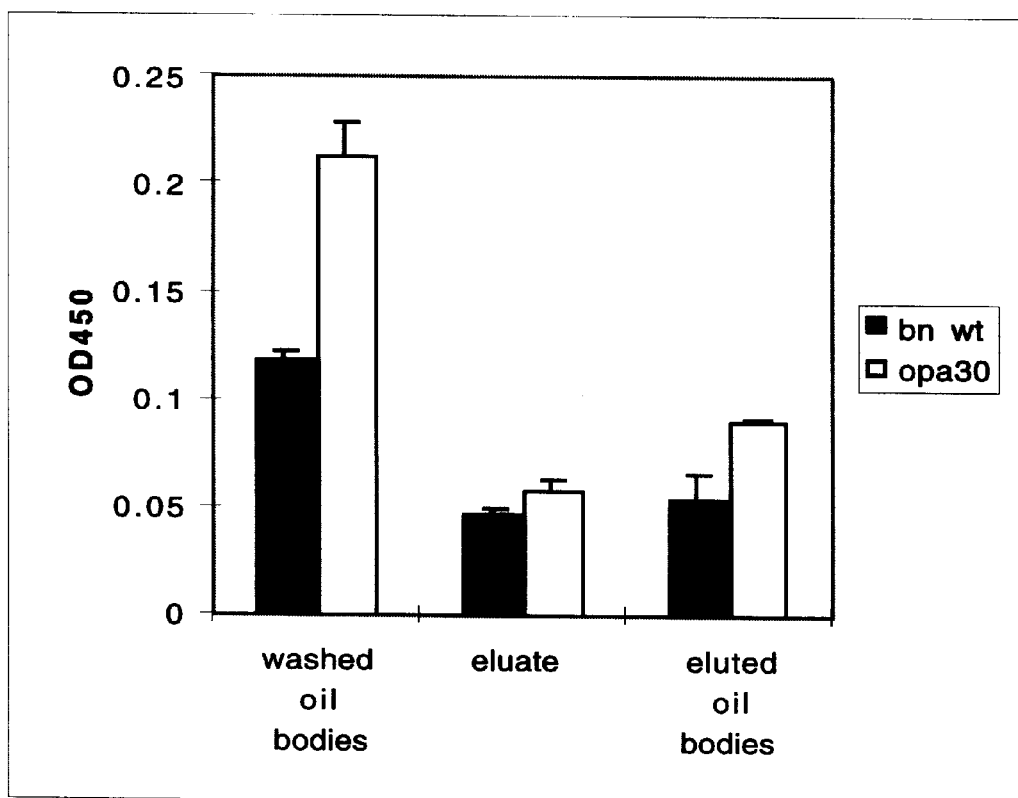
FIG. 17 illustrates binding and elution of IgGs to oil bodies isolated from wildtype *B. napus* (bn wt) and a transgenic *B. napus* line, expressing an oleosin protein A fusions. Error bars represent the results from 4 independent experiments.

In order to elute the IgGs from the oil bodies, the washed oil body preparation was resuspended in 100 mM glycine pH 3.0 and centrifuged for 15 min at 16,000×g and incubated for 30' at room temperature. Following neutralization in 500 μl 100 mM Tris-Cl pH 8.0, both the oil body fraction and the eluate were assayed for HRP activity as above. The binding and elution of IgGs to oil bodies from weld type *B. napus* and transgenic *B. napus* expressing an oleosin protein A fusion, are illustrated in FIG. 17.

All publications, patents and patent applications are herein incorporated by reference in their entirety to the same extent as if each individual publication, patent or patent application was specifically and individually indicated to be incorporated by reference in its entirety.

We claim:

1. A method for the separation of a target molecule from a sample comprising:
   1) contacting (i) oil bodies with (ii) a sample containing the target molecule to allow the target molecule to associate with the oil bodies; and
   2) separating the oil bodies associated with the target molecule thereby separating the target molecule from the sample.

2. A method according to claim 1 further comprising a ligand molecule that associates with the oil bodies and the target molecule.

3. A method according to claim 2 wherein the ligand molecule is covalently attached to the oil bodies.

4. A method according to claim 3 wherein the ligand molecule is covalently attached to an oil body protein in the oil bodies.

5. A method according to claim 2 wherein the ligand is comprised of two molecules, a first molecule that associates with the oil bodies and a second molecule that associates with the target, wherein the first molecule and the second molecule associate with each other.

6. A method according to claim 5 wherein the first and second ligand molecules are conjugated to each other.

7. A method according to claim 4 wherein the ligand molecule is a protein.

8. A method according to claim 7 wherein the protein ligand is a fusion protein with the oil body protein.

9. A method according to claim 1 wherein the target molecule is selected from the group consisting of proteins, peptides, organic molecules, lipids, carbohydrates, nucleic acids, cells, cell organelles, cell fragments, viruses, metals and ions.

10. A method according to claim 8 wherein the ligand molecule is hirudin and the target molecule is thrombin.

11. A method according to claim 8 wherein the ligand molecule is protein A and the target molecule an immunoglobulin.

12. A method according to claim 8 wherein the ligand molecule is metallothionein and the target molecule is cadmium.

13. A method according to claim 8 wherein the ligand molecule is a cellulose binding protein and the target molecule is cellulose.

14. A method according to claim 8 wherein the ligand molecule is a nucleic acid binding protein and the target molecule is a nucleic acid.

15. A method according to claim 14 wherein the ligand is a single stranded DNA binding protein or an RNA binding protein and the target is a single stranded nucleic acid molecule.

16. A method according to claim 2 wherein the ligand is an antibody that binds to the oil body or an oil body protein.

17. A method according to claim 16 wherein the target is a cell, cell organelle or cell fragment capable of binding the ligand antibody.

18. A method according to claim 16 wherein the cell is *Staphylococcus aureus*.

19. A method according to claim 16 wherein the ligand is a bivalent antibody that binds to both the oil body and the target.

20. A method according to any one of claim 6 wherein the ligand is an antibody conjugated to avidin and the target molecule is biotin.

21. A method according to claim 4 wherein the oil body protein is an oleosin.

22. A method according to claim 21 wherein the oleosin is derived from a plant selected from the group consisting of rapeseed (Brassica spp.), soybean (*Glycine max*), sunflower (*Helianthus annuus*), oil palm (*Elaeis guineeis*), coconut (*Cocus nucifera*), castor (*Ricinus communis*), safflower (*Carthamus tinctorius*), mustard (Brassica spp. and *Sinapis alba*), coriander (*Coriandrum sativum*) linseed/flax (*Linum usitatissimum*), thale cress (*Arabidopsis thaliana*) and maize (*Zea mays*).

23. A method according to claim 1 wherein in step 1) the oil bodies and the sample are mixed and then incubated for about 1 minute to about 24 hours.

24. A method according to claim 23 wherein the mixed oil bodies and sample are incubated at a temperature range from 4° C. to room temperature.

25. A method according to claim 1 wherein the oil bodies associated with the target molecule are separated from the sample in step (2) by centrifugation, floatation or size exclusion.

26. A method according to claim 1, further comprising 3) separating the target molecule from the oil bodies.

27. A method according to claim 26 wherein the target molecule is separated by elution under appropriate conditions.

28. A method according to claim 1 wherein the oil bodies are obtained from the group of plants consisting of rapeseed (Brassica spp.), soybean (*Glycine max*), sunflower (*Helianthus annuus*), oil palm (*Elaeis guineeis*), coconut (*Cocus nucifera*), castor (*Ricinus communis*), safflower (*Carthamus tinctorius*), mustard (Brassica spp. and *Sinapis alba*), coriander (*Coriandrum sativum*) linseed/flax (*Linum usitatissimum*), thale cress (*Arabidopsis thaliana*) and maize (*Zea mays*).

* * * * *

SEQUENCE LISTING

<160> NUMBER OF SEQ ID NOS: 14

<210> SEQ ID NO 1
<211> LENGTH: 522
<212> TYPE: DNA
<213> ORGANISM: Arabidopsis Thaliana
<220> FEATURE:
<221> NAME/KEY: CDS
<222> LOCATION: (1)..(522)
<223> OTHER INFORMATION:

<400> SEQUENCE: 1

```
atg gcg gat aca gct aga gga acc cat cac gat atc atc ggc aga gac       48
Met Ala Asp Thr Ala Arg Gly Thr His His Asp Ile Ile Gly Arg Asp
1               5                   10                  15 cag tac ccg atg atg ggc cga gac cga gac cag tac cag atg tcc gga       96
Gln Tyr Pro Met Met Gly Arg Asp Arg Asp Gln Tyr Gln Met Ser Gly
            20                  25                  30 cga gga tct gac tac tcc aag tct agg cag att gct aaa gct gca act      144
Arg Gly Ser Asp Tyr Ser Lys Ser Arg Gln Ile Ala Lys Ala Ala Thr
        35                  40                  45 gct gtc aca gct ggt ggt tcc ctc ctt gtt ctc tcc agc ctt acc ctt      192
Ala Val Thr Ala Gly Gly Ser Leu Leu Val Leu Ser Ser Leu Thr Leu
    50                  55                  60 gtt gga act gtc ata gct ttg act gtt gca aca cct ctg ctc gtt atc      240
Val Gly Thr Val Ile Ala Leu Thr Val Ala Thr Pro Leu Leu Val Ile
65                  70                  75                  80 ttc agc cca atc ctt gtc ccg gct ctc atc aca gtt gca ctc ctc atc      288
Phe Ser Pro Ile Leu Val Pro Ala Leu Ile Thr Val Ala Leu Leu Ile
                85                  90                  95 acc ggt ttt ctt tcc tct gga ggg ttt ggc att gcc gct ata acc gtt      336
Thr Gly Phe Leu Ser Ser Gly Gly Phe Gly Ile Ala Ala Ile Thr Val
            100                 105                 110 ttc tct tgg att tac aag tac gca acg gga gag cac cca cag gga tca      384
Phe Ser Trp Ile Tyr Lys Tyr Ala Thr Gly Glu His Pro Gln Gly Ser
        115                 120                 125 gac aag ttg gac agt gca agg atg aag ttg gga agc aaa gct cag gat      432
Asp Lys Leu Asp Ser Ala Arg Met Lys Leu Gly Ser Lys Ala Gln Asp
    130                 135                 140 ctg aaa gac aga gct cag tac tac gga cag caa cat act ggt ggg gaa      480
Leu Lys Asp Arg Ala Gln Tyr Tyr Gly Gln Gln His Thr Gly Gly Glu
145                 150                 155                 160 cat gac cgt gac cgt act cgt ggt ggc cag cac act act taa              522
His Asp Arg Asp Arg Thr Arg Gly Gly Gln His Thr Thr
                165                 170
```

-continued

```
<210> SEQ ID NO 2
<211> LENGTH: 173
<212> TYPE: PRT
<213> ORGANISM: Arabidopsis Thaliana

<400> SEQUENCE: 2
```

Met Ala Asp Thr Ala Arg Gly Thr His His Asp Ile Ile Gly Arg Asp
1               5                   10                  15

Gln Tyr Pro Met Met Gly Arg Asp Arg Asp Gln Tyr Gln Met Ser Gly
            20                  25                  30

Arg Gly Ser Asp Tyr Ser Lys Ser Arg Gln Ile Ala Lys Ala Ala Thr
        35                  40                  45

Ala Val Thr Ala Gly Gly Ser Leu Leu Val Leu Ser Ser Leu Thr Leu
    50                  55                  60

Val Gly Thr Val Ile Ala Leu Thr Val Ala Thr Pro Leu Leu Val Ile
65                  70                  75                  80

Phe Ser Pro Ile Leu Val Pro Ala Leu Ile Thr Val Ala Leu Leu Ile
                85                  90                  95

Thr Gly Phe Leu Ser Ser Gly Gly Phe Gly Ile Ala Ala Ile Thr Val
            100                 105                 110

Phe Ser Trp Ile Tyr Lys Tyr Ala Thr Gly Glu His Pro Gln Gly Ser
        115                 120                 125

Asp Lys Leu Asp Ser Ala Arg Met Lys Leu Gly Ser Lys Ala Gln Asp
    130                 135                 140

Leu Lys Asp Arg Ala Gln Tyr Tyr Gly Gln Gln His Thr Gly Gly Glu
145                 150                 155                 160

His Asp Arg Asp Arg Thr Arg Gly Gly Gln His Thr Thr
                165                 170

```
<210> SEQ ID NO 3
<211> LENGTH: 2115
<212> TYPE: DNA
<213> ORGANISM: Artificial Sequence
<220> FEATURE:
<223> OTHER INFORMATION: Oleosin - Hirudin Fusion
<221> NAME/KEY: CDS
<222> LOCATION: (862)..(1215)
<223> OTHER INFORMATION:
<221> NAME/KEY: CDS
<222> LOCATION: (1456)..(1833)
<223> OTHER INFORMATION:

<400> SEQUENCE: 3
ctatacccaa cctcggtctt ggtcacacca ggaactctct ggtaagctag ctccactccc      60
cagaaacaac cggcgccaaa ttgccggaat tgctgacctg aagacggaac atcatcgtcg     120
ggtccttggg cgattgcggc ggaagatggg tcagcttggg cttgaggacg agacccgaat    180
cgagtctgtt gaaaggttgt tcattgggat ttgtatacga agattggtcg tcgagaggtt    240
tgagggaaag gacaaatggg tttggctctg gagaaagaga gtgcggcttt agagagagaa    300
ttgagaggtt tagagagaga tgcggcggcg atgacgggag gagagacgac gaggacctgc    360
attatcaaag cagtgacgtg gtgaaatttg aacttttaa gaggcagata gatttattat     420
ttgtatccat tttcttcatt gttctagaat gtcgcggaac aaattttaaa actaaatcct    480
aaattttct aattttgttg ccaatagtgg atatgtgggc cgtatagaag gaatctattg     540
aaggcccaaa cccatactga cgagcccaaa ggttcgtttt gcgttttatg tttcggttcg    600
atgccaacgc cacattctga gctaggcaaa aaacaaacgt gtctttgaat agactcctct    660

```

```
cgttaacaca tgcagcggct gcatggtgac gccattaaca cgtggcctac aattgcatga        720
tgtctccatt gacacgtgac ttctcgtctc ctttcttaat atatctaaca aacactccta        780
cctcttccaa aatatataca catcttttg atcaatctct cattcaaaat ctcattctct         840
ctagtaaaca agaacaaaaa a atg gcg gat aca gct aga gga acc cat cac          891
                        Met Ala Asp Thr Ala Arg Gly Thr His His
                         1               5                  10 gat atc atc ggc aga gac cag tac ccg atg atg ggc cga gac cga gac          939
Asp Ile Ile Gly Arg Asp Gln Tyr Pro Met Met Gly Arg Asp Arg Asp
             15                  20                  25 cag tac cag atg tcc gga cga gga tct gac tac tcc aag tct agg cag          987
Gln Tyr Gln Met Ser Gly Arg Gly Ser Asp Tyr Ser Lys Ser Arg Gln
         30                  35                  40 att gct aaa gct gca act gct gtc aca gct ggt ggt tcc ctc ctt gtt         1035
Ile Ala Lys Ala Ala Thr Ala Val Thr Ala Gly Gly Ser Leu Leu Val
     45                  50                  55 ctc tcc agc ctt acc ctt gtt gga act gtc ata gct ttg act gtt gca         1083
Leu Ser Ser Leu Thr Leu Val Gly Thr Val Ile Ala Leu Thr Val Ala
 60                  65                  70 aca cct ctg ctc gtt atc ttc agc cca atc ctt gtc ccg gct ctc atc         1131
Thr Pro Leu Leu Val Ile Phe Ser Pro Ile Leu Val Pro Ala Leu Ile
 75                  80                  85                  90 aca gtt gca ctc ctc atc acc ggt ttt ctt tcc tct gga ggg ttt ggc         1179
Thr Val Ala Leu Leu Ile Thr Gly Phe Leu Ser Ser Gly Gly Phe Gly
             95                 100                 105 att gcc gct ata acc gtt ttc tct tgg att tac aag taagcacaca              1225
Ile Ala Ala Ile Thr Val Phe Ser Trp Ile Tyr Lys
        110                 115 tttatcatct tacttcataa ttttgtgcaa tatgtgcatg catgtgttga gccagtagct       1285
ttggatcaat ttttttggtc gaataacaaa tgtaacaata agaaattgca aattctaggg       1345
aacatttggt taactaaata cgaaatttga cctagctagc ttgaatgtgt ctgtgtatat       1405
catctatata ggtaaaatgc ttggtatgat acctattgat tgtgaatagg tac gca          1461
                                                         Tyr Ala
                                                         120 acg gga gag cac cca cag gga tca gac aag ttg gac agt gca agg atg         1509
Thr Gly Glu His Pro Gln Gly Ser Asp Lys Leu Asp Ser Ala Arg Met
             125                 130                 135 aag ttg gga agc aaa gct cag gat ctg aaa gac aga gct cag tac tac         1557
Lys Leu Gly Ser Lys Ala Gln Asp Leu Lys Asp Arg Ala Gln Tyr Tyr
         140                 145                 150 gga cag caa cat act ggt tgg gaa cat gac cgt gac cgt act cgt ggt         1605
Gly Gln Gln His Thr Gly Trp Glu His Asp Arg Asp Arg Thr Arg Gly
     155                 160                 165 ggc cag cac act act gcg atc gaa ggg aga atc act tac act gac tgt         1653
Gly Gln His Thr Thr Ala Ile Glu Gly Arg Ile Thr Tyr Thr Asp Cys
 170                 175                 180 act gaa tct gga cag aac ctc tgt ctc tgt gaa gga tct aac gtt tgt         1701
Thr Glu Ser Gly Gln Asn Leu Cys Leu Cys Glu Gly Ser Asn Val Cys
185                 190                 195                 200 gga aag gga aac aag tgt atc ctc gga tct aac gga aag gga aac cag         1749
Gly Lys Gly Asn Lys Cys Ile Leu Gly Ser Asn Gly Lys Gly Asn Gln
             205                 210                 215 tgt gtt act gga gaa gga act cca aac cca gaa tct cac aac aac gga         1797
Cys Val Thr Gly Glu Gly Thr Pro Asn Pro Glu Ser His Asn Asn Gly
         220                 225                 230 gac ttc gaa gaa atc cct gaa gaa tac ctc cag taa gtcgactcta              1843
Asp Phe Glu Glu Ile Pro Glu Glu Tyr Leu Gln
```

```
                235                  240
gacggatctc ccgatcgttc aaacatttgg caataaagtt tcttaagatt gaatcctgtt      1903
gccggtcttg cgatgattat catataattt ctgttgaatt acgttaagca tgtaataatt      1963
aacatgtaat gcatgacgtt atttatgaga tgggttttta tgattagagt cccgcaatta      2023
tacatttaat acgcgataga aaacaaaata tagcgcgcaa actaggataa attatcgcgc      2083
gcggtgtcat ctatgttact agatcggaat tc                                    2115
```

```
<210> SEQ ID NO 4
<211> LENGTH: 118
<212> TYPE: PRT
<213> ORGANISM: Artificial Sequence
<220> FEATURE:
<223> OTHER INFORMATION: Oleosin - Hirudin Fusion

<400> SEQUENCE: 4

Met Ala Asp Thr Ala Arg Gly Thr His His Asp Ile Ile Gly Arg Asp
 1               5                  10                  15

Gln Tyr Pro Met Met Gly Arg Asp Arg Asp Gln Tyr Gln Met Ser Gly
            20                  25                  30

Arg Gly Ser Asp Tyr Ser Lys Ser Arg Gln Ile Ala Lys Ala Ala Thr
        35                  40                  45

Ala Val Thr Ala Gly Gly Ser Leu Leu Val Leu Ser Ser Leu Thr Leu
    50                  55                  60

Val Gly Thr Val Ile Ala Leu Thr Val Ala Thr Pro Leu Leu Val Ile
65                  70                  75                  80

Phe Ser Pro Ile Leu Val Pro Ala Leu Ile Thr Val Ala Leu Leu Ile
                85                  90                  95

Thr Gly Phe Leu Ser Ser Gly Gly Phe Gly Ile Ala Ala Ile Thr Val
            100                 105                 110

Phe Ser Trp Ile Tyr Lys
            115
```

```
<210> SEQ ID NO 5
<211> LENGTH: 125
<212> TYPE: PRT
<213> ORGANISM: Artificial Sequence
<220> FEATURE:
<223> OTHER INFORMATION: Oleosin - Hirudin Fusion

<400> SEQUENCE: 5

Tyr Ala Thr Gly Glu His Pro Gln Gly Ser Asp Lys Leu Asp Ser Ala
 1               5                  10                  15

Arg Met Lys Leu Gly Ser Lys Ala Gln Asp Leu Lys Asp Arg Ala Gln
            20                  25                  30
Tyr Tyr Gly Gln Gln His Thr Gly Trp Glu His Asp Arg Asp Arg Thr 35                  40                  45
Arg Gly Gly Gln His Thr Thr Ala Ile Glu Gly Arg Ile Thr Tyr Thr
    50                  55                  60

Asp Cys Thr Glu Ser Gly Gln Asn Leu Cys Leu Cys Glu Gly Ser Asn
65                  70                  75                  80
Val Cys Gly Lys Gly Asn Lys Cys Ile Leu Gly Ser Asn Gly Lys Gly 85                  90                  95
Asn Gln Cys Val Thr Gly Glu Gly Thr Pro Asn Pro Glu Ser His Asn
            100                 105                 110

Asn Gly Asp Phe Glu Glu Ile Pro Glu Glu Tyr Leu Gln
            115                 120                 125
```

-continued

```
<210> SEQ ID NO 6
<211> LENGTH: 2366
<212> TYPE: DNA
<213> ORGANISM: Artificial Sequence
<220> FEATURE:
<223> OTHER INFORMATION: Oleosin - Metallothionein Fusion
<221> NAME/KEY: CDS
<222> LOCATION: (1092)..(1856)
<223> OTHER INFORMATION:

<400> SEQUENCE: 6
```

| | |
|---|---|
| gagctcaaat acgatctgat actgataacg tctagatttt tagggttaaa gcaatcaatc | 60 |
| acctgacgat tcaaggtggt tggatcatga cgattccaga aaacatcaag caagctctca | 120 |
| aagctacact ctttgggatc atactgaact ctaacaacct cgttatgtcc cgtagtgcca | 180 |
| gtacagacat cctcgtaact cggattatgc acgatgccat ggctataccc aacctcggtc | 240 |
| ttggtcacac caggaactct ctggtaagct agctccactc cccagaaaca accggcgcca | 300 |
| aattgccgga attgctgacc tgaagacgga acatcatcgt cgggtccttg ggcgattgcg | 360 |
| gcggaagatg ggtcagcttg gcttgagga cgagaccccga atcgagtctg ttgaaaggtt | 420 |
| gttcattggg atttgtatac ggagattggt cgtcgagagg tttgagggaa aggacaaatg | 480 |
| ggtttggctc tggagaaaga gagtgcggct ttagagagag aattgagagg tttagagaga | 540 |
| gatgcggcgg cgatgacggg aggagagacg acgaggacct gcattatcaa agcagtgacg | 600 |
| tggtgaaatt tggaactttt aagaggcaga tagatttatt atttgtatcc attttcttca | 660 |
| ttgttctaga atgtcgcgga acaaatttta aaactaaatc ctaattttt ctaattttgt | 720 |
| tgccaatagt ggatatgtgg gccgtataga aggaatctat tgaaggccca aacccatact | 780 |
| gacgagccca aaggttcgtt ttgcgttta tgtttcggtt cgatgccaac gccacattct | 840 |
| gagctaggca aaaacaaac gtgtctttga atagactcct ctcgttaaca catgcagcgg | 900 |
| ctgcatggtg acgccattaa cacgtggcct acaattgcat gatgtctcca ttgacacgtg | 960 |
| acttctcgtc tcctttctta atatatctaa caaacactcc tacctcttcc aaaatatata | 1020 |
| cacatctttt tgatcaatct ctcattcaaa atctcattct ctctagtaaa caggatcccc | 1080 |

| | | |
|---|---|---|
| ctcgcggccg c atg gcg gat aca gct aga acc cat cac gat gtc aca agt | | 1130 |
| Met Ala Asp Thr Ala Arg Thr His His Asp Val Thr Ser | | |
| 1 5 10 | | |

| | | |
|---|---|---|
| cga gat cag tat ccc cga gac cga gac cag tat tct atg atc ggt cga | | 1178 |
| Arg Asp Gln Tyr Pro Arg Asp Arg Asp Gln Tyr Ser Met Ile Gly Arg | | |
| 15 20 25 | | |

| | | |
|---|---|---|
| gac cgt gac cag tac tct atg atg ggc cga gac cga gac cag tac aac | | 1226 |
| Asp Arg Asp Gln Tyr Ser Met Met Gly Arg Asp Arg Asp Gln Tyr Asn | | |
| 30 35 40 45 | | |

| | | |
|---|---|---|
| atg tat ggt cga gac tac tcc aag tct aga cag att gct aag gct gtt | | 1274 |
| Met Tyr Gly Arg Asp Tyr Ser Lys Ser Arg Gln Ile Ala Lys Ala Val | | |
| 50 55 60 | | |

| | | |
|---|---|---|
| acc gca gtc acg gcg ggt ggg tcc ctc ctt gtc ctc tcc agt ctc acc | | 1322 |
| Thr Ala Val Thr Ala Gly Gly Ser Leu Leu Val Leu Ser Ser Leu Thr | | |
| 65 70 75 | | |

| | | |
|---|---|---|
| ctt gtt ggt act gtc att gct ttg act gtt gcc act cca ctc ctc gtt | | 1370 |
| Leu Val Gly Thr Val Ile Ala Leu Thr Val Ala Thr Pro Leu Leu Val | | |
| 80 85 90 | | |

| | | |
|---|---|---|
| atc ttt agc cca atc ctc gtg ccg gct ctc atc acc gta gca ctt ctc | | 1418 |
| Ile Phe Ser Pro Ile Leu Val Pro Ala Leu Ile Thr Val Ala Leu Leu | | |
| 95 100 105 | | |

| | | |
|---|---|---|
| atc act ggc ttt ctc tcc tct ggt ggg ttt gcc att gca gct ata acc | | 1466 |
| Ile Thr Gly Phe Leu Ser Ser Gly Gly Phe Ala Ile Ala Ala Ile Thr | | |
| 110 115 120 125 | | |

-continued

```
gtc ttc tcc tgg atc tat aag tac gca acg gga gag cac cca cag ggg      1514
Val Phe Ser Trp Ile Tyr Lys Tyr Ala Thr Gly Glu His Pro Gln Gly
            130                 135                 140 tca gat aag ttg gac agt gca agg atg aag ctg gga acc aaa gct cag      1562
Ser Asp Lys Leu Asp Ser Ala Arg Met Lys Leu Gly Thr Lys Ala Gln
145                 150                 155 gat att aaa gac aga gct caa tac tac gga cag caa cat aca ggt ggt      1610
Asp Ile Lys Asp Arg Ala Gln Tyr Tyr Gly Gln Gln His Thr Gly Gly
            160                 165                 170 gag cat gac cgt gac cgt act cgt ggt ggc cag cac act act ctc gtt      1658
Glu His Asp Arg Asp Arg Thr Arg Gly Gly Gln His Thr Thr Leu Val
175                 180                 185 cca cga gga tcc atg gat ccc aac tgc tcc tgt gcc gcc agt gac tcc      1706
Pro Arg Gly Ser Met Asp Pro Asn Cys Ser Cys Ala Ala Ser Asp Ser
190                 195                 200                 205 tgc acc tgc gcc ggc tcc tgc aag tgc aaa gag tgc aaa tgc acc tcc      1754
Cys Thr Cys Ala Gly Ser Cys Lys Cys Lys Glu Cys Lys Cys Thr Ser
            210                 215                 220 tgc aag aaa agc tgc tgc tcc tgc tgt cct gtg ggc tgt gcc aag tgt      1802
Cys Lys Lys Ser Cys Cys Ser Cys Cys Pro Val Gly Cys Ala Lys Cys
225                 230                 235 gcc cag ggc tgc atc tgc aaa ggg gcg tcg gac aag tgc agc tgc tgt      1850
Ala Gln Gly Cys Ile Cys Lys Gly Ala Ser Asp Lys Cys Ser Cys Cys
            240                 245                 250 gcc tga gcggccgcga gggctgcaga atgagttcca agatggtttg tgacgaagtt      1906
Ala agttggttgt ttttatggaa ctttgtttaa gcttgtaatg tggaaagaac gtgtggcttt      1966
gtggttttta aatgttggtg aataaagatg tttcctttgg attaactagt attttcctta      2026
ttggtttcat ggttttagca cacaacattt taaatatgct gttagatgat atgctgcctg      2086
ctttattatt tacttacccc tcaccttcag tttcaaagtt gttgcaatga ctctgtgtag      2146
tttaagatcg agtgaaagta gattttgtct atatttatta ggggtatttg atatgctaat      2206
ggtaaacatg gttatgaca gcgtactttt ttggttatgg tgttgacgtt ccttttaaa       2266 cattatagta gcgtccttgg tctgtgttca ttggttgaac aaaggcacac tcacttggag      2326
atgccgtctc cactgatatt tgaacaaaga attcggtacc                           2366
```

<210> SEQ ID NO 7
<211> LENGTH: 254
<212> TYPE: PRT
<213> ORGANISM: Artificial Sequence
<220> FEATURE:
<223> OTHER INFORMATION: Oleosin - Metallothionein Fusion

<400> SEQUENCE: 7

```
Met Ala Asp Thr Ala Arg Thr His His Asp Val Thr Ser Arg Asp Gln
1               5                   10                  15

Tyr Pro Arg Asp Arg Asp Gln Tyr Ser Met Ile Gly Arg Asp Arg Asp
                20                  25                  30

Gln Tyr Ser Met Met Gly Arg Asp Arg Asp Gln Tyr Asn Met Tyr Gly
            35                  40                  45

Arg Asp Tyr Ser Lys Ser Arg Gln Ile Ala Lys Ala Val Thr Ala Val
        50                  55                  60

Thr Ala Gly Gly Ser Leu Leu Val Leu Ser Ser Leu Thr Leu Val Gly
65                  70                  75                  80

Thr Val Ile Ala Leu Thr Val Ala Thr Pro Leu Leu Val Ile Phe Ser
                85                  90                  95
```

```
Pro Ile Leu Val Pro Ala Leu Ile Thr Val Ala Leu Leu Ile Thr Gly
            100                 105                 110

Phe Leu Ser Ser Gly Gly Phe Ala Ile Ala Ala Ile Thr Val Phe Ser
            115                 120                 125

Trp Ile Tyr Lys Tyr Ala Thr Gly Glu His Pro Gln Gly Ser Asp Lys
            130                 135             140

Leu Asp Ser Ala Arg Met Lys Leu Gly Thr Lys Ala Gln Asp Ile Lys
145                 150                 155                 160

Asp Arg Ala Gln Tyr Tyr Gly Gln Gln His Thr Gly Gly Glu His Asp
                165                 170                 175

Arg Asp Arg Thr Arg Gly Gly Gln His Thr Thr Leu Val Pro Arg Gly
            180                 185                 190

Ser Met Asp Pro Asn Cys Ser Cys Ala Ala Ser Asp Ser Cys Thr Cys
            195                 200                 205

Ala Gly Ser Cys Lys Cys Lys Glu Cys Lys Cys Thr Ser Cys Lys Lys
            210                 215                 220

Ser Cys Cys Ser Cys Cys Pro Val Gly Cys Ala Lys Cys Ala Gln Gly
225                 230                 235                 240

Cys Ile Cys Lys Gly Ala Ser Asp Lys Cys Ser Cys Cys Ala
                245                 250

<210> SEQ ID NO 8
<211> LENGTH: 804
<212> TYPE: DNA
<213> ORGANISM: Artificial Sequence
<220> FEATURE:
<223> OTHER INFORMATION: Protein A Primers
<221> NAME/KEY: CDS
<222> LOCATION: (5)..(796)
<223> OTHER INFORMATION:

<400> SEQUENCE: 8 ctcc atg gat caa cgc aat ggt ttt atc caa agc ctt aaa gat gat cca      49
     Met Asp Gln Arg Asn Gly Phe Ile Gln Ser Leu Lys Asp Asp Pro
     1               5                   10                  15 agc caa agt gct aac gtt tta ggt gaa gct caa aaa ctt aat gac tct      97
Ser Gln Ser Ala Asn Val Leu Gly Glu Ala Gln Lys Leu Asn Asp Ser
                20                  25                  30 caa gct cca aaa gct gat gcg caa caa aat aac ttc aac aaa gat caa     145
Gln Ala Pro Lys Ala Asp Ala Gln Gln Asn Asn Phe Asn Lys Asp Gln
            35                  40                  45 caa agc gcc ttc tat gaa atc ttg aac atg cct aac tta aac gaa gcg     193
Gln Ser Ala Phe Tyr Glu Ile Leu Asn Met Pro Asn Leu Asn Glu Ala
        50                  55                  60 caa cgt aac ggc ttc att caa agt ctt aaa gac gac cca agc caa agc     241
Gln Arg Asn Gly Phe Ile Gln Ser Leu Lys Asp Asp Pro Ser Gln Ser
    65                  70                  75 act aac gtt tta ggt gaa gct aaa aaa tta aac gaa tct caa gca ccg     289
Thr Asn Val Leu Gly Glu Ala Lys Lys Leu Asn Glu Ser Gln Ala Pro
80                  85                  90                  95 aaa gct gat aac aat ttc aac aaa gaa caa caa aat gct ttc tat gaa     337
Lys Ala Asp Asn Asn Phe Asn Lys Glu Gln Gln Asn Ala Phe Tyr Glu
                100                 105                 110 atc ttg aat atg cct aac tta aac gaa gaa caa cgc aat ggt ttc atc     385
Ile Leu Asn Met Pro Asn Leu Asn Glu Glu Gln Arg Asn Gly Phe Ile
            115                 120                 125 caa agc tta aaa gat gac cca agc caa agt gct aac cta ttg tca gaa     433
Gln Ser Leu Lys Asp Asp Pro Ser Gln Ser Ala Asn Leu Leu Ser Glu
        130                 135                 140
```

-continued

```
gct aaa aag tta aat gaa tct caa gca ccg aaa gcg gat aac aaa ttc     481
Ala Lys Lys Leu Asn Glu Ser Gln Ala Pro Lys Ala Asp Asn Lys Phe
    145                 150                 155 aac aaa gaa caa caa aat gct ttc tat gaa atc tta cat tta cct aac     529
Asn Lys Glu Gln Gln Asn Ala Phe Tyr Glu Ile Leu His Leu Pro Asn
160                 165                 170                 175 tta aac gaa gaa caa cgc aat ggt ttc atc caa agc cta aaa gat gac     577
Leu Asn Glu Glu Gln Arg Asn Gly Phe Ile Gln Ser Leu Lys Asp Asp
                180                 185                 190 cca agc caa agc gct aac ctt tta gca gaa gct aaa aag cta aat gat     625
Pro Ser Gln Ser Ala Asn Leu Leu Ala Glu Ala Lys Lys Leu Asn Asp
            195                 200                 205 gct caa gca cca aaa gct gac aac aaa ttc aac aaa gaa caa caa aat     673
Ala Gln Ala Pro Lys Ala Asp Asn Lys Phe Asn Lys Glu Gln Gln Asn
        210                 215                 220 gct ttc tat gaa att tta cat tta cct aac tta act gaa gaa caa cgt     721
Ala Phe Tyr Glu Ile Leu His Leu Pro Asn Leu Thr Glu Glu Gln Arg
    225                 230                 235 aac ggc ttc atc caa agc ctt aaa gac gat ccg ggg aat tcc cgg gga     769
Asn Gly Phe Ile Gln Ser Leu Lys Asp Asp Pro Gly Asn Ser Arg Gly
240                 245                 250                 255 tcc gtc gac ctg cag ata aca aat tag aagcttgc                        804
Ser Val Asp Leu Gln Ile Thr Asn
                260
```

<210> SEQ ID NO 9
<211> LENGTH: 263
<212> TYPE: PRT
<213> ORGANISM: Artificial Sequence
<220> FEATURE:
<223> OTHER INFORMATION: Protein A Primers

<400> SEQUENCE: 9

```
Met Asp Gln Arg Asn Gly Phe Ile Gln Ser Leu Lys Asp Asp Pro Ser
1               5                   10                  15

Gln Ser Ala Asn Val Leu Gly Glu Ala Gln Lys Leu Asn Asp Ser Gln
            20                  25                  30

Ala Pro Lys Ala Asp Ala Gln Gln Asn Phe Asn Lys Asp Gln Gln
        35                  40                  45

Ser Ala Phe Tyr Glu Ile Leu Asn Met Pro Asn Leu Asn Glu Ala Gln
    50                  55                  60

Arg Asn Gly Phe Ile Gln Ser Leu Lys Asp Asp Pro Ser Gln Ser Thr
65                  70                  75                  80

Asn Val Leu Gly Glu Ala Lys Lys Leu Asn Glu Ser Gln Ala Pro Lys
            85                  90                  95

Ala Asp Asn Asn Phe Asn Lys Glu Gln Gln Asn Ala Phe Tyr Glu Ile
        100                 105                 110

Leu Asn Met Pro Asn Leu Asn Glu Gln Arg Asn Gly Phe Ile Gln
    115                 120                 125

Ser Leu Lys Asp Asp Pro Ser Gln Ser Ala Asn Leu Leu Ser Glu Ala
    130                 135                 140

Lys Lys Leu Asn Glu Ser Gln Ala Pro Lys Ala Asp Asn Lys Phe Asn
145                 150                 155                 160

Lys Glu Gln Gln Asn Ala Phe Tyr Glu Ile Leu His Leu Pro Asn Leu
                165                 170                 175

Asn Glu Glu Gln Arg Asn Gly Phe Ile Gln Ser Leu Lys Asp Asp Pro
            180                 185                 190
```

```
Ser Gln Ser Ala Asn Leu Leu Ala Glu Ala Lys Lys Leu Asn Asp Ala
        195                 200                 205

Gln Ala Pro Lys Ala Asp Asn Lys Phe Asn Lys Glu Gln Gln Asn Ala
        210                 215                 220

Phe Tyr Glu Ile Leu His Leu Pro Asn Leu Thr Glu Glu Gln Arg Asn
225                 230                 235                 240

Gly Phe Ile Gln Ser Leu Lys Asp Asp Pro Gly Asn Ser Arg Gly Ser
                245                 250                 255

Val Asp Leu Gln Ile Thr Asn
            260

<210> SEQ ID NO 10
<211> LENGTH: 26
<212> TYPE: DNA
<213> ORGANISM: Artificial Sequence
<220> FEATURE:
<223> OTHER INFORMATION: Primer Bk 266

<400> SEQUENCE: 10
tccatggatc aacgcaatgg tttatc                                    26

<210> SEQ ID NO 11
<211> LENGTH: 29
<212> TYPE: DNA
<213> ORGANISM: Artificial Sequence
<220> FEATURE:
<223> OTHER INFORMATION: Primer Bk 267

<400> SEQUENCE: 11
gcaagcttct aatttgttat ctgcaggtc                                 29

<210> SEQ ID NO 12
<211> LENGTH: 2709
<212> TYPE: DNA
<213> ORGANISM: Artificial Sequence
<220> FEATURE:
<223> OTHER INFORMATION: Oleosin - Protein A Fusion
<221> NAME/KEY: CDS
<222> LOCATION: (868)..(1218)
<223> OTHER INFORMATION:
<221> NAME/KEY: CDS
<222> LOCATION: (1462)..(2433)
<223> OTHER INFORMATION:

<400> SEQUENCE: 12
ccatggctat acccaacctc ggtcttggtc acaccaggaa ctctctggta agctagctcc     60
actccccaga acaaccggc gccaaattgc cggaattgct gacctgaaga cggaacatca    120
tcgtcgggtc cttgggcgat tgcggcggaa gatgggtcag cttgggcttg aggacgagac    180
ccgaatcgag tctgttgaaa ggttgttcat tgggatttgt atacggagat tggtcgtcga    240
gaggtttgag ggaaaggaca atgggtttg gctctggaga agagagtgc ggctttagag      300 agagaattga gaggtttaga gagagatgcg gcggcgatga cgggaggaga gacgacgagg    360
acctgcatta tcaaagcagt gacgtggtga aatttggaac ttttaagagg cagatagatt    420
tattatttgt atccattttc ttcattgttc tagaatgtcg cggaacaaat tttaaaacta    480
aatcctaaat ttttctaatt ttgttgccaa tagtggatat gtgggccgta tagaaggaat    540
ctattgaagg cccaaaccca tactgacgag cccaaaggtt cgttttgcgt tttatgtttc    600
ggttcgatgc caacgccaca ttctgagcta ggcaaaaaac aaacgtgtct ttgaatagac    660
tcctctcgtt aacacatgca gcggctgcat ggtgacgcca ttaacacgtg gcctacaatt    720
```

-continued

```
gcatgatgtc tccattgaca cgtgacttct cgtctccttt cttaatatat ctaacaaaca    780
ctcctacctc ttccaaaata tatacacatc tttttgatca atctctcatt caaaatctca    840
ttctctctag taaacaagaa caaaaaa atg gcg gat aca gct aga gga acc cat    894
                               Met Ala Asp Thr Ala Arg Gly Thr His
                               1               5 cac gat atc atc ggc aga gac cag tac ccg atg atg ggc cga gac cga     942
His Asp Ile Ile Gly Arg Asp Gln Tyr Pro Met Met Gly Arg Asp Arg
10               15                  20                  25 gac cag tac cag atg tcc gga cga gga tct gac tac tcc aag tct agg     990
Asp Gln Tyr Gln Met Ser Gly Arg Gly Ser Asp Tyr Ser Lys Ser Arg
                30                  35                  40 cag att gct aaa gct gca act gct gtc aca gct ggt ggt tcc ctc ctt    1038
Gln Ile Ala Lys Ala Ala Thr Ala Val Thr Ala Gly Gly Ser Leu Leu
         45                  50                  55 gtt ctc tcc agc ctt acc ctt gtt gga act gtc ata gct ttg act gtt    1086
Val Leu Ser Ser Leu Thr Leu Val Gly Thr Val Ile Ala Leu Thr Val
        60                  65                  70 gca aca cct ctg ctc gtt atc ttc agc cca atc ctt gtc ccg gct ctc    1134
Ala Thr Pro Leu Leu Val Ile Phe Ser Pro Ile Leu Val Pro Ala Leu
75                  80                  85 atc aca gtt gca ctc ctc atc acc ggt ttt ctt tcc tct gga ggg ttt    1182
Ile Thr Val Ala Leu Leu Ile Thr Gly Phe Leu Ser Ser Gly Gly Phe
90                  95                 100                 105 ggc att gcc gct ata acc gtt ttc tct tgg att tac aagtaagcac         1228
Gly Ile Ala Ala Ile Thr Val Phe Ser Trp Ile Tyr
             110                 115 acatttatca tcttacttca taattttgtg caatatgtgc atgcatgtgt tgagccagta   1288
gctttggatc aattttttg gtcgaataac aaatgtaaca ataagaaatt gcaaattcta    1348
gggaacattt ggttaactaa atacgaaatt tgacctagct agcttgaatg tgtctgtgta   1408
tatcatctat ataggtaaaa tgcttggtat gatacctatt gattgtgaat agg tac     1464
                                                           Tyr gca acg gga gag cac cca cag gga tca gac aag ttg gac agt gca agg    1512
Ala Thr Gly Glu His Pro Gln Gly Ser Asp Lys Leu Asp Ser Ala Arg
         120                 125                 130 atg aag ttg gga agc aaa gct cag gat ctg aaa gac aga gct cag tac    1560
Met Lys Leu Gly Ser Lys Ala Gln Asp Leu Lys Asp Arg Ala Gln Tyr
135                 140                 145                 150 tac gga cag caa cat act ggt ggg gaa cat gac cgt gac cgt act cgt    1608
Tyr Gly Gln Gln His Thr Gly Gly Glu His Asp Arg Asp Arg Thr Arg
                155                 160                 165 ggt ggc cag cac act act ctc gtt cca cga gga tcc atg gat caa cgc    1656
Gly Gly Gln His Thr Thr Leu Val Pro Arg Gly Ser Met Asp Gln Arg
         170                 175                 180 aat ggt ttt atc caa agc ctt aaa gat gat cca agc caa agt gct aac    1704
Asn Gly Phe Ile Gln Ser Leu Lys Asp Asp Pro Ser Gln Ser Ala Asn
185                 190                 195 gtt tta ggt gaa gct caa aaa ctt aat gac tct caa gct cca aaa gct    1752
Val Leu Gly Glu Ala Gln Lys Leu Asn Asp Ser Gln Ala Pro Lys Ala
        200                 205                 210 gat gcg caa caa aat aac ttc aac aaa gat caa caa agc gcc ttc tat    1800
Asp Ala Gln Gln Asn Asn Phe Asn Lys Asp Gln Gln Ser Ala Phe Tyr
215                 220                 225                 230 gaa atc ttg aac atg cct aac tta aac gaa gcg caa cgt aac ggc ttc    1848
Glu Ile Leu Asn Met Pro Asn Leu Asn Glu Ala Gln Arg Asn Gly Phe
                235                 240                 245 att caa agt ctt aaa gac gac cca agc caa agc act aac gtt tta ggt    1896
Ile Gln Ser Leu Lys Asp Asp Pro Ser Gln Ser Thr Asn Val Leu Gly
```

```
                 250                 255                 260
gaa gct aaa aaa tta aac gaa tct caa gca ccg aaa gct gat aac aat    1944
Glu Ala Lys Lys Leu Asn Glu Ser Gln Ala Pro Lys Ala Asp Asn Asn
            265                 270                 275 ttc aac aaa gaa caa caa aat gct ttc tat gaa atc ttg aat atg cct    1992
Phe Asn Lys Glu Gln Gln Asn Ala Phe Tyr Glu Ile Leu Asn Met Pro
        280                 285                 290 aac tta aac gaa gaa caa cgc aat ggt ttc atc caa agc tta aaa gat    2040
Asn Leu Asn Glu Glu Gln Arg Asn Gly Phe Ile Gln Ser Leu Lys Asp
295                 300                 305                 310 gac cca agc caa agt gct aac cta ttg tca gaa gct aaa aag tta aat    2088
Asp Pro Ser Gln Ser Ala Asn Leu Leu Ser Glu Ala Lys Lys Leu Asn
                315                 320                 325 gaa tct caa gca ccg aaa gcg gat aac aaa ttc aac aaa gaa caa caa    2136
Glu Ser Gln Ala Pro Lys Ala Asp Asn Lys Phe Asn Lys Glu Gln Gln
            330                 335                 340 aat gct ttc tat gaa atc tta cat tta cct aac tta aac gaa gaa caa    2184
Asn Ala Phe Tyr Glu Ile Leu His Leu Pro Asn Leu Asn Glu Glu Gln
        345                 350                 355 cgc aat ggt ttc atc caa agc cta aaa gat gac cca agc caa agc gct    2232
Arg Asn Gly Phe Ile Gln Ser Leu Lys Asp Asp Pro Ser Gln Ser Ala
360                 365                 370 aac ctt tta gca gaa gct aaa aag cta aat gat gct caa gca cca aaa    2280
Asn Leu Leu Ala Glu Ala Lys Lys Leu Asn Asp Ala Gln Ala Pro Lys
375                 380                 385                 390 gct gac aac aaa ttc aac aaa gaa caa caa aat gct ttc tat gaa att    2328
Ala Asp Asn Lys Phe Asn Lys Glu Gln Gln Asn Ala Phe Tyr Glu Ile
                395                 400                 405 tta cat tta cct aac tta act gaa gaa caa cgt aac ggc ttc atc caa    2376
Leu His Leu Pro Asn Leu Thr Glu Glu Gln Arg Asn Gly Phe Ile Gln
            410                 415                 420 agc ctt aaa gac gat ccg ggg aat tcc cgg gga tcc gtc gac ctg cag    2424
Ser Leu Lys Asp Asp Pro Gly Asn Ser Arg Gly Ser Val Asp Leu Gln
        425                 430                 435 ata aca aat tagaagcttg catgcctgca ggtcgatcgt tcaaacattt            2473
Ile Thr Asn
    440 ggcaataaag tttcttaaga ttgaatcctg ttgccggtct tgcgatgatt atcatataat  2533 ttctgttgaa ttcgttaag catgtaataa ttaacatgta atgcatgacg ttatttatga  2593 gatgggtttt tatgattaga gtcccgcaat tatacattta atacgcgata gaaaacaaaa  2653 tatagcgcgc aaactaggat aaattatcgc gcgcggtgtc atctatgtta ctagat      2709
```

<210> SEQ ID NO 13
<211> LENGTH: 117
<212> TYPE: PRT
<213> ORGANISM: Artificial Sequence
<220> FEATURE:
<223> OTHER INFORMATION: Oleosin - Protein A Fusion

<400> SEQUENCE: 13

```
Met Ala Asp Thr Ala Arg Gly Thr His His Asp Ile Ile Gly Arg Asp
1               5                   10                  15

Gln Tyr Pro Met Met Gly Arg Asp Arg Asp Gln Tyr Gln Met Ser Gly
            20                  25                  30

Arg Gly Ser Asp Tyr Ser Lys Ser Arg Gln Ile Ala Lys Ala Ala Thr
        35                  40                  45

Ala Val Thr Ala Gly Gly Ser Leu Leu Val Leu Ser Ser Leu Thr Leu
    50                  55                  60
```

```
Val Gly Thr Val Ile Ala Leu Thr Val Ala Thr Pro Leu Leu Val Ile
 65                  70                  75                  80

Phe Ser Pro Ile Leu Val Pro Ala Leu Ile Thr Val Ala Leu Leu Ile
                 85                  90                  95

Thr Gly Phe Leu Ser Ser Gly Gly Phe Gly Ile Ala Ala Ile Thr Val
            100                 105                 110

Phe Ser Trp Ile Tyr
            115

<210> SEQ ID NO 14
<211> LENGTH: 324
<212> TYPE: PRT
<213> ORGANISM: Artificial Sequence
<220> FEATURE:
<223> OTHER INFORMATION: Oleosin - Protein A Fusion

<400> SEQUENCE: 14

Tyr Ala Thr Gly Glu His Pro Gln Gly Ser Asp Lys Leu Asp Ser Ala
  1               5                  10                  15

Arg Met Lys Leu Gly Ser Lys Ala Gln Asp Leu Lys Asp Arg Ala Gln
             20                  25                  30

Tyr Tyr Gly Gln Gln His Thr Gly Gly Glu His Asp Arg Asp Arg Thr
            35                  40                  45

Arg Gly Gly Gln His Thr Thr Leu Val Pro Arg Gly Ser Met Asp Gln
 50                  55                  60

Arg Asn Gly Phe Ile Gln Ser Leu Lys Asp Asp Pro Ser Gln Ser Ala
 65                  70                  75                  80

Asn Val Leu Gly Glu Ala Gln Lys Leu Asn Asp Ser Gln Ala Pro Lys
             85                  90                  95

Ala Asp Ala Gln Gln Asn Asn Phe Asn Lys Asp Gln Gln Ser Ala Phe
            100                 105                 110

Tyr Glu Ile Leu Asn Met Pro Asn Leu Asn Glu Ala Gln Arg Asn Gly
            115                 120                 125

Phe Ile Gln Ser Leu Lys Asp Asp Pro Ser Gln Ser Thr Asn Val Leu
130                 135                 140

Gly Glu Ala Lys Lys Leu Asn Glu Ser Gln Ala Pro Lys Ala Asp Asn
145                 150                 155                 160

Asn Phe Asn Lys Glu Gln Gln Asn Ala Phe Tyr Glu Ile Leu Asn Met
                165                 170                 175

Pro Asn Leu Asn Glu Glu Gln Arg Asn Gly Phe Ile Gln Ser Leu Lys
                180                 185                 190

Asp Asp Pro Ser Gln Ser Ala Asn Leu Leu Ser Glu Ala Lys Lys Leu
            195                 200                 205

Asn Glu Ser Gln Ala Pro Lys Ala Asp Asn Lys Phe Asn Lys Glu Gln
210                 215                 220

Gln Asn Ala Phe Tyr Glu Ile Leu His Leu Pro Asn Leu Asn Glu Glu
225                 230                 235                 240

Gln Arg Asn Gly Phe Ile Gln Ser Leu Lys Asp Asp Pro Ser Gln Ser
                245                 250                 255

Ala Asn Leu Leu Ala Glu Ala Lys Lys Leu Asn Asp Ala Gln Ala Pro
            260                 265                 270

Lys Ala Asp Asn Lys Phe Asn Lys Glu Gln Gln Asn Ala Phe Tyr Glu
            275                 280                 285

Ile Leu His Leu Pro Asn Leu Thr Glu Glu Gln Arg Asn Gly Phe Ile
290                 295                 300
```

-continued

```
Gln Ser Leu Lys Asp Asp Pro Gly Asn Ser Arg Gly Ser Val Asp Leu
305                 310                 315                 320
Gln Ile Thr Asn
```